(12) United States Patent
Richard et al.

(10) Patent No.: US 8,738,339 B2
(45) Date of Patent: May 27, 2014

(54) SYSTEM AND METHOD FOR ULTRASONIC TESTING

(75) Inventors: Daniel Richard, Quebec City (CA); Dirk Verspeelt, Gentbrugge (BE); Frederic Morrow, Quebec City (CA); Guy Maes, Quebec City (CA); Jean-Francois Tremblay, Quebec City (CA); Martin Garneau, Quebec City (CA); Stephane Turgeon, St-Nicolas (CA); Alexandre Charlebois, Quebec City (CA)

(73) Assignee: Zetec, Inc., Snoqualmie, WA (US)

( * ) Notice: Subject to any disclaimer, the term of this patent is extended or adjusted under 35 U.S.C. 154(b) by 1059 days.

(21) Appl. No.: 12/588,114

(22) Filed: Oct. 5, 2009

(65) Prior Publication Data

US 2010/0094606 A1    Apr. 15, 2010

Related U.S. Application Data

(60) Provisional application No. 61/136,801, filed on Oct. 3, 2008.

(30) Foreign Application Priority Data

Oct. 3, 2008  (CA) ........................... 2640462

(51) Int. Cl.
| | |
|---|---|
| G06F 7/60 | (2006.01) |
| G06G 7/48 | (2006.01) |
| G01B 5/28 | (2006.01) |
| G01H 1/08 | (2006.01) |
| G01N 9/24 | (2006.01) |
| G01N 29/00 | (2006.01) |

(52) U.S. Cl.
USPC .......... 703/6; 703/2; 702/39; 73/593; 73/606; 73/626; 73/628

(58) Field of Classification Search
None
See application file for complete search history.

(56) References Cited

U.S. PATENT DOCUMENTS

| | | | | |
|---|---|---|---|---|
| 6,202,489 | B1 | 3/2001 | Beffy et al. | |
| 6,789,427 | B2 * | 9/2004 | Batzinger et al. | 73/614 |
| 7,234,354 | B2 * | 6/2007 | Barshinger et al. | 73/619 |
| 7,263,888 | B2 * | 9/2007 | Barshinger et al. | 73/606 |
| 7,305,885 | B2 * | 12/2007 | Barshinger et al. | 73/602 |
| 7,581,296 | B2 * | 9/2009 | Yetter et al. | 29/25.35 |
| 2004/0020296 | A1 * | 2/2004 | Moles et al. | 73/627 |
| 2006/0283250 | A1 | 12/2006 | Fair et al. | |

FOREIGN PATENT DOCUMENTS

EP    1524519 A1    4/2005

OTHER PUBLICATIONS

Syed, Camran: International Search Report from corresponding PCT Application No. PCT/CA2009/001381: Search completed Feb. 15, 2010.

* cited by examiner

*Primary Examiner* — Omar Fernandez Rivas
*Assistant Examiner* — Nithya J Moll
(74) *Attorney, Agent, or Firm* — Caesar, Rivise, Bernstein, Cohen & Pokotilow, Ltd.

(57) ABSTRACT

A method of establishing position dependent focal laws and dynamically accessing these focal laws during inspection is disclosed comprising the steps of partitioning a CAD model into distinct geometric regions prior to inspection, generating a dedicated set of focal laws for each of the geometric regions, and associating each position of the scanner with one of the geometric regions. A method of compressing an A-Scan using a windowing technique is also disclosed. Additionally, methods for computing and displaying volumetric slices in real-time are disclosed. Finally, a method of firing multiple probes at different firing frequencies is disclosed, as well as a multi-probe inspection system that enables parallel firing.

12 Claims, 18 Drawing Sheets

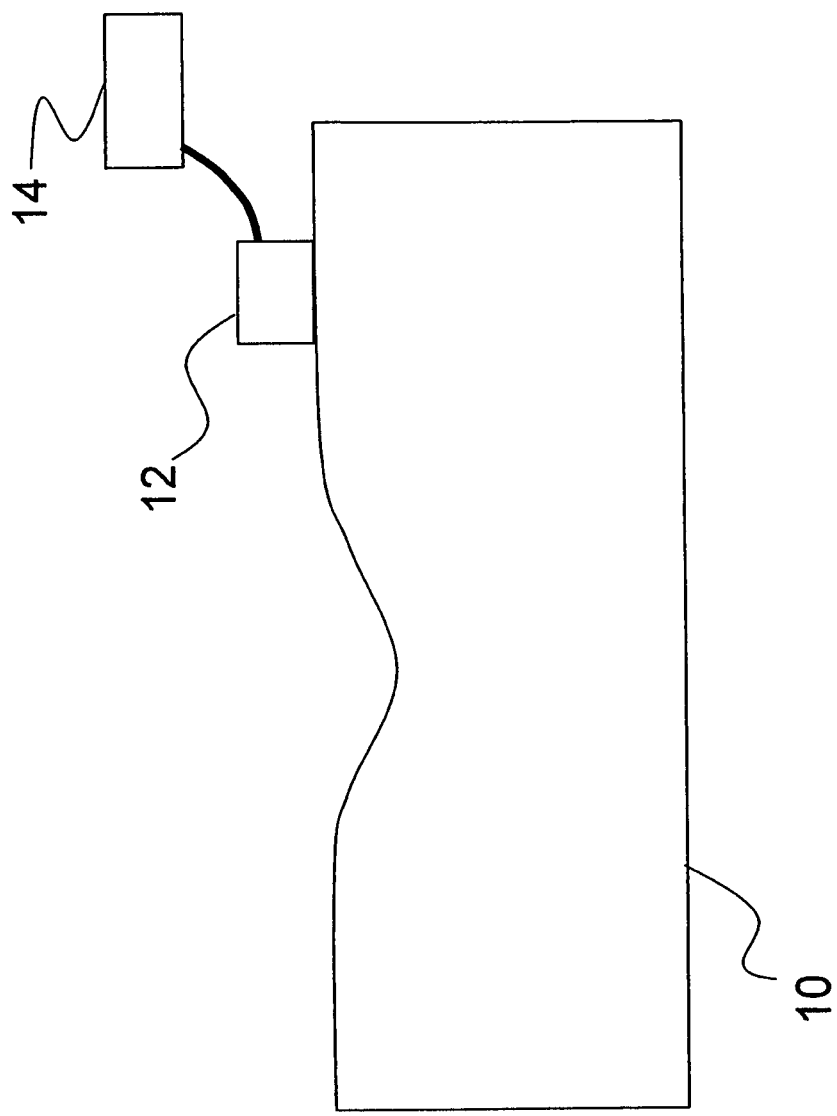
Figure 1-A

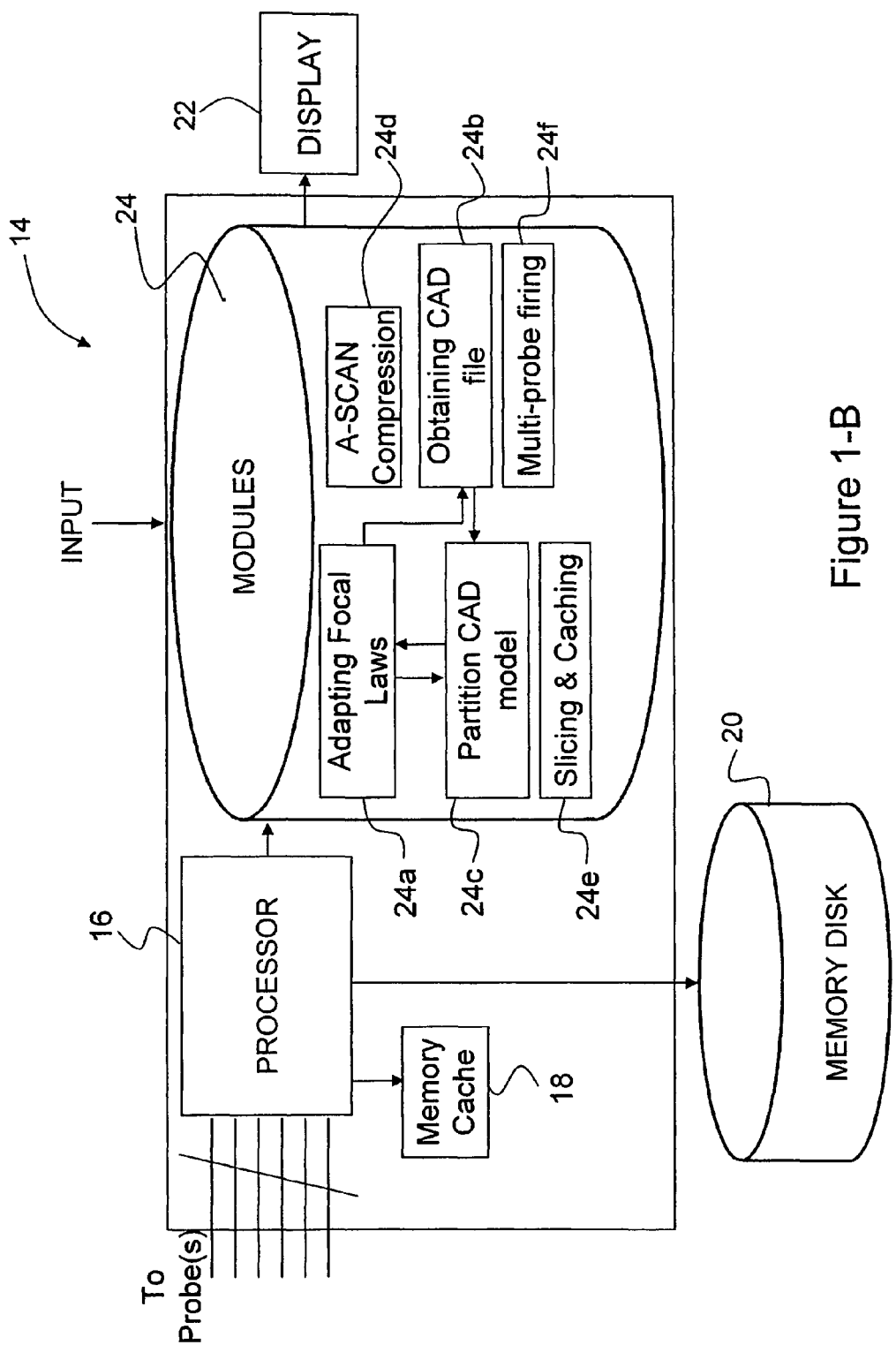
Figure 1-B

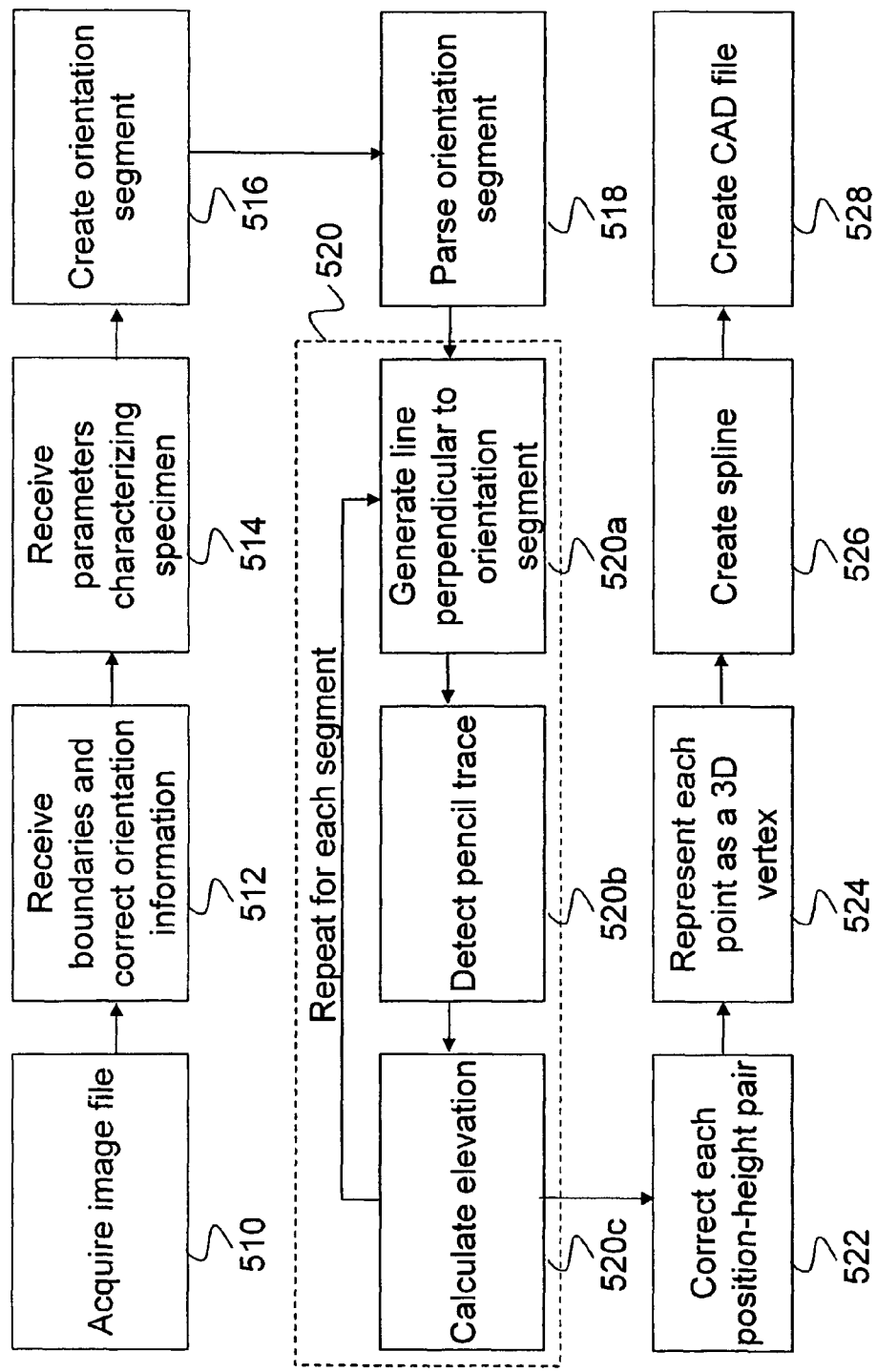
Figure 5-A

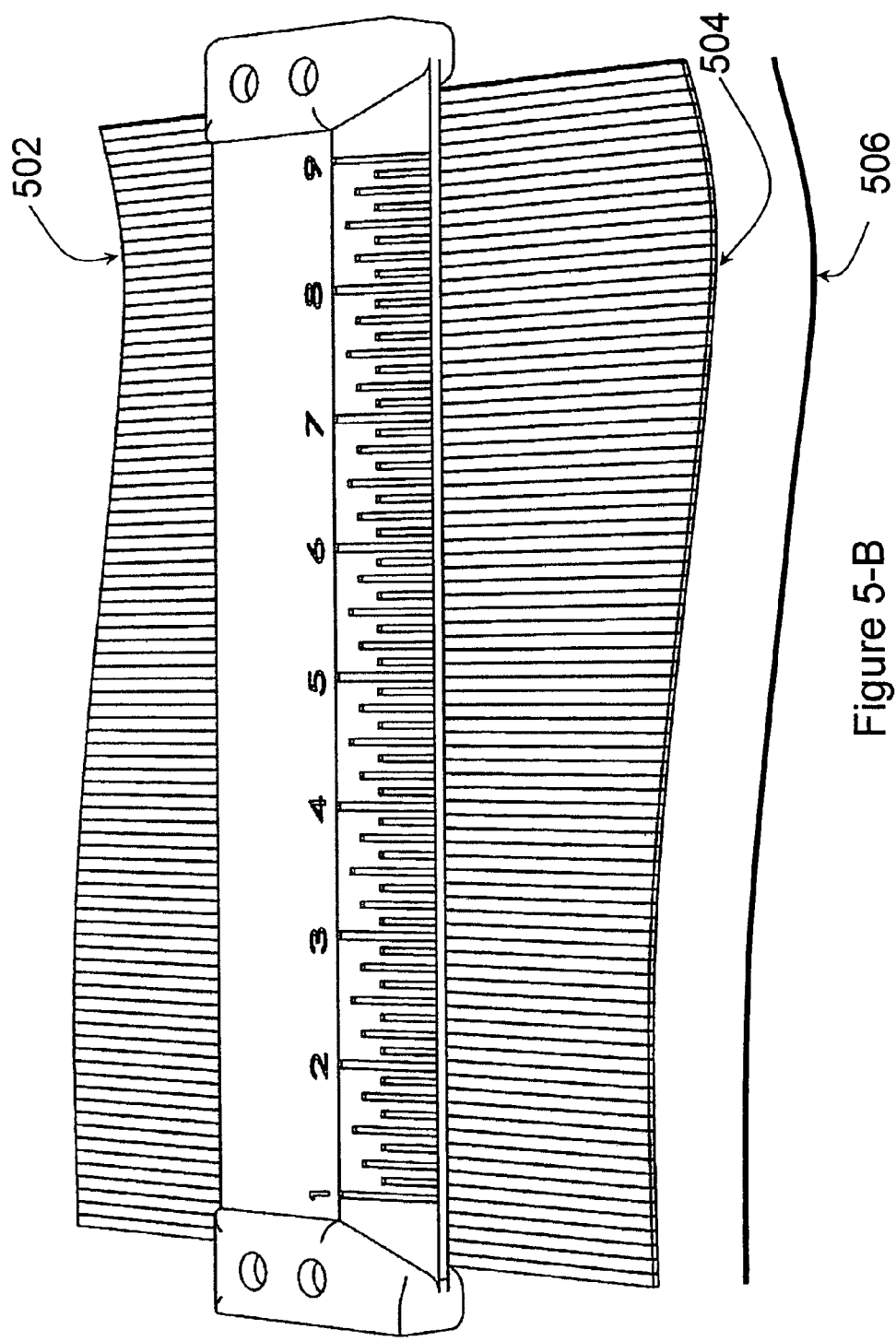
Figure 5-B

SYSTEM AND METHOD FOR ULTRASONIC TESTING

CROSS-REFERENCE TO RELATED APPLICATIONS

This application claims priority from U.S. Provisional Application Ser. No. 61/136,801 filed Oct. 3, 2008, and Canadian Patent Application No. 2,640,462, filed Oct. 3, 2008. The contents of both of these applications is incorporated herein by reference.

FIELD OF THE INVENTION

The present invention relates generally to ultrasonic testing.

DESCRIPTION OF THE PRIOR ART

Ultrasonic testing is a type of nondestructive testing used to examine, characterize and/or detect flaws in a material specimen. Sound energy is introduced into the specimen and propagates through the specimen in the form of waves. When there is a discontinuity in the wave path due to a flaw or other discontinuity in the specimen, some of the energy will be reflected back. By measuring the time of the received echo and its amplitude, the depth and nature of the discontinuity may be characterized. For example, it is often desired to inspect a weld between two objects, such as a pair of pipes, to search for a crack in the weld. Using ultrasonic testing, pulses of sound energy are introduced into the weld. For each pulse, the time and amplitude of the return echo, if any, is used in characterizing the crack.

An improvement over traditional ultrasonic testing is to use phased array ultrasonic testing. In traditional ultrasonic testing, a monocrystal probe acts as a transducer to emit a divergent wave and receive the echo. Sometimes dual-element probes (one for transmitting and one for receiving) or a monocrystal probe with focused lenses are used. However, in any case, the ultrasonic field propagates only along a single acoustic axis with a single refracted angle. Such a scanning pattern has limited detection and sizing capabilities. Phased array ultrasonic testing, on the other hand, uses an array or matrix of small piezocomposite elements in a single housing to produce a sequence of waves that interfere to generate an overall wave front or beam with a particular angle and/or focal depth. While the probe remains in a single spot, the angle and/or focal depth of the beam is varied or steered to scan the below region and provide a characterization of any discontinuities. The steering and focussing of the ultrasonic field beam provides a better inspection of the scanned region than that produced by a divergent ultrasonic wave propagating along a single refracted angle.

The scanning provided by the probe is controlled by a set of focal laws. Each focal law defines the timing of the pulsing of each element to produce a beam with a given angle and/or focal depth. A set of focal laws acts to steer and vary the focus of the beam. For example, the beam may be swept through an angular range focused at a specific depth. In this case, each focal law would define an angle in the sweep, and the number of angular increments would be equal to the number of focal laws. As another example, the probe may consist of a single array of elements, and a focal law may be sequenced to produce a simple linear sectorial scan. The focal law could be programmed to use only a subset of the elements to form the aperture, and the aperture could be multiplexed across the array. The returned data from each firing would then be merged to form a cross-sectional image of the region below the probe.

For specimens that have a geometry that is constant over the whole scanning region, a dedicated set of focal laws can be utilized, which do not need to be adapted as the probe is moved along the surface of the specimen. However, for specimens in which the geometry is not constant over the whole scanning region, it is desired and often necessary to update the focal laws when the probe moves from one region to another. Otherwise, error will be introduced and the accuracy of the scan will be compromised. Developing position dependent focal law firing is a challenging problem. It is known in the art, for example, to attempt to address the problem by continually adapting the focal laws as the probe moves during the inspection process. Such a solution results in an increased inspection time since the updated focal laws must be calculated as the inspection progresses. This is particularly undesirable if the specimen is unable to perform its dedicated function while an inspection is occurring.

As explained above, during the inspection of a specimen, each time an ultrasonic beam is fired into the specimen an echo may be produced, which will return at a given time and with a given amplitude. The return time and amplitude of the echo is used in characterizing and measuring the depth of the discontinuity. The vector of the received amplitude of the echo at each measured time interval is referred to as an A-scan. If traditional ultrasonic testing is utilized, the designated receiver captures the received amplitude of the return echo at each time interval. Alternatively, if phased array ultrasonic testing is utilized, at each time interval each element receives part of the returned echo. The echoes measured at each element are time-shifted and combined according to the focal law. However, regardless of whether traditional ultrasonic testing or phased array ultrasonic testing is used, the resulting A-scan will be a vector with a length equal to the number of measured time units and a value of the amplitude of the returned echo at each time unit. As will be appreciated, during the scanning process a large number of A-scans are collected, and such a large amount of data is a challenge to store and analyze. Therefore, it is desired to compress an A-scan in order to reduce the amount of data to be stored and analyzed, while at the same time retaining the important information in the A-scan. Various techniques are known in the art for compressing an A-scan, some of which attempt to identify and retain only the high peaks in the signal. However, such algorithms generally identify peaks in terms of the subsequent drop in signal amplitude, which does not ensure that all the highest peaks will be captured.

During the scanning process, ultrasonic beams are fired into the specimen and data is collected, which may be stored in the form of A-scans or the like. The large amount of data collected during the scanning process is often manipulated by software to construct 3-D images and/or 2-D volumetric slices of the specimen once scanning is complete. This allows a user to easily visualize and characterize any flaw or discontinuity in the specimen. Due to the large amounts of data to be manipulated, current ultrasonic testing equipment is only able to access, manipulate, and display relatively small amounts of data in real-time. To access, manipulate and display large amounts of data (e.g. greater than 1 GB), delayed processing and image construction is often necessary. For example, if a user desires to view a volumetric slice through a 3-D representation of the specimen, the amount of time required by the software to retrieve the data from the memory/disk drive and construct the volumetric view may cause the user to experience a noticeable delay. Such delays are particularly pronounced when the amount data representing the 3-D volume is large.

Finally, when scanning a specimen, it is often desirable to perform scanning using a scanner having multiple probes mounted on it. Assuming the system is able to accommodate the increased data throughput of using multiple probes, the inspection time will generally be reduced. For example, in scanning a weld connecting a pair of pipes, the apparatus performing the scan may use a first probe to move along the weld on one pipe and simultaneously use a second probe to move along the weld on the other pipe. The data from both probes would be collected and utilized by the system to detect and characterize any cracks present in the weld. Sometimes the probes used by the system may have different physical characteristics (e.g. a different number of elements or a different size of probe), and/or the probes may generate different beam sizes to focus at different depths or inspect smaller or larger volumes within the specimen. Regardless, each probe is fired at the same frequency, which may result in collecting redundant data. Additionally, the firing of each probe is traditionally performed sequentially during each acquisition cycle.

It is an object of the present invention to address at least some of the above disadvantages.

SUMMARY OF THE INVENTION

In one aspect of the invention there is provided a method of establishing position dependent focal laws for the ultrasonic inspection of a specimen with complex geometry, the method being performed by a dedicated module located on a computing device and comprising the steps of: (a) the dedicated module loading a computer model of the specimen into a portion of memory; (b) the dedicated module partitioning the model into distinct regions; (c) the dedicated module generating a distinct set of focal laws for each of the distinct regions; and (d) the dedicated module associating each position of a scanner with at least one of the distinct regions and storing the association in memory; whereby during subsequent ultrasonic inspection of the specimen, each position of the scanner utilizes the distinct set of focal laws associated with the at least one region.

In another aspect of the invention there is provided a method of generating customized two-dimensional slices of a three-dimensional data structure, the three-dimensional data structure representing the surface of the scanned specimen along two axes and the received ultrasonic amplitude data along a third axis, the method being performed by a dedicated module located on a computing device and comprising the steps of: (a) the dedicated module defining a first directional view along a first axis of the data structure and creating a first set of constituent slices, wherein each constituent slice in the first set comprises amplitude data projected between first and second planes intersecting the first axis; (b) the dedicated module defining a second directional view along a second axis of the data structure and creating a second set of constituent slices, wherein each constituent slice in the second set comprises amplitude data projected between first and second planes intersecting the second axis; (c) the dedicated module defining a third directional view along a third axis of the data structure and creating a third set of constituent slices, wherein each constituent slice in the third set comprises amplitude data projected between first and second planes intersecting the third axis; (d) the dedicated module receiving a request indicating a directional view selected from either the first directional view, the second directional view, or the third directional view, the request also indicating boundaries on the axis associated with the indicated directional view; (e) the dedicated module selecting a subset of constituent slices, the subset comprising one or more constituent slices within the boundaries on the associated axis; (f) the dedicated module defining an intermediate portion of the associated axis; (g) the dedicated module generating one or more intermediate slices on the intermediate portion, wherein each intermediate slice comprises amplitude data projected between first and second planes intersecting the associated axis in the intermediate portion; and (h) the dedicated module merging the subset of constituent slices with the one or more intermediate slices to create a customized slice.

In yet another aspect of the invention, there is provided a method of generating a computer-aided-design (CAD) model from a position C-Scan of a specimen, the position C-Scan comprising a set of values with each value representing a position on the surface of the specimen and an associated height measurement, the method being performed by a dedicated module located on a computing device and comprising the steps of: (a) the dedicated module loading the position C-Scan into a portion of memory; (b) the dedicated module receiving parameters characterizing the specimen; (c) the dedicated module converting each value of the C-Scan into representation as a vertex; and (d) the dedicated module using the parameters characterizing the specimen and the vertex values to generate a CAD file.

In still another aspect of the invention, there is provided a method of generating a computer-aided-design (CAD) model from an image file of a trace made using a manual profiling tool, the method being performed by a dedicated module located on a computing device and comprising the steps of: (a) the dedicated module loading the image into a portion of memory; (b) the dedicated module receiving parameters characterizing the specimen; (c) the dedicated module parsing the trace into discrete sections, each parsed section having an associated position value; (d) for each parsed section, the dedicated module calculating the elevation of the parsed section; (e) for each parsed section, the dedicated module converting the position value and the elevation into representation as a vertex; and (f) the dedicated module using the parameters characterizing the specimen and the vertex values to generate a CAD file.

In another aspect of the invention, there is provided a method of compressing an A-scan, the A-scan being represented as a vector in which each vector position represents a position in time with each position having an associated amplitude value, the method being performed by a dedicated module located on a computing device and comprising the steps of: (a) the dedicated module establishing a first window spanning a length equal to a first number of positions, a second window spanning a length equal to a second number of positions, and a second vector for storing the compressed A-scan; and (b) beginning at a first position in the vector and progressing towards a second position, the dedicated module: (i) searching in the first window for a peak amplitude value; (ii) saving in memory the peak amplitude value and its associated position; (iii) searching in a second window for an amplitude value exceeding the peak amplitude value, the second window beginning adjacent to the associated position of the peak amplitude value; and (iv) if an amplitude value exceeding the peak amplitude value is found in step (iii), setting the amplitude value exceeding the peak value as the peak amplitude value and repeating steps (ii) to (iv); otherwise, storing the peak amplitude value and its associated position in the second vector, moving to a position adjacent the second window, and returning to step (i).

In yet another aspect of the invention there is provided a method of independently firing N probes on a multi-probe scanner, where N is greater than one (N>1), the method being performed by a dedicated module located on a computing device and comprising the steps of: (a) providing instructions to move the scanner to a first scanner position and fire at least some of the N probes; (b) providing instructions to move the scanner to an adjacent scanner position; and (c) for each probe of the N probes: (i) determining whether the adjacent probe position covers volume in the specimen not included in the previous firing; and (ii) instructing the probe to fire if the adjacent probe position covers volume not included in the previous firing.

In still another aspect of the invention there is provided a system for providing parallel firing of two or more probes comprising: (a) an independent module associated with elements of each probe, each of the independent modules comprising a first unit for storing focal laws and firing the associated elements according to the focal laws, a digitizer for converting received amplitude data into a digital form, and a second unit for storing the digital amplitude data; and (b) a processing unit connected to each independent module; whereby the each independent module operates independently of the other modules and communicates its stored digital amplitude data to the processing unit.

BRIEF DESCRIPTION OF THE DRAWINGS

Exemplary embodiments of the invention will now be described by way of example only with reference to the accompanying drawings, in which:

FIGS. 1-A and 1-B show a schematic of a system for performing ultrasonic testing;

FIG. 5-A is a schematic diagram of a set of computer executable instructions for an embodiment of a method of generating a CAD file from the image of a trace made using a manual profiling tool;

FIG. 5-B shows a manual profiling tool;

DETAILED DESCRIPTION OF THE INVENTION

Figure 2:
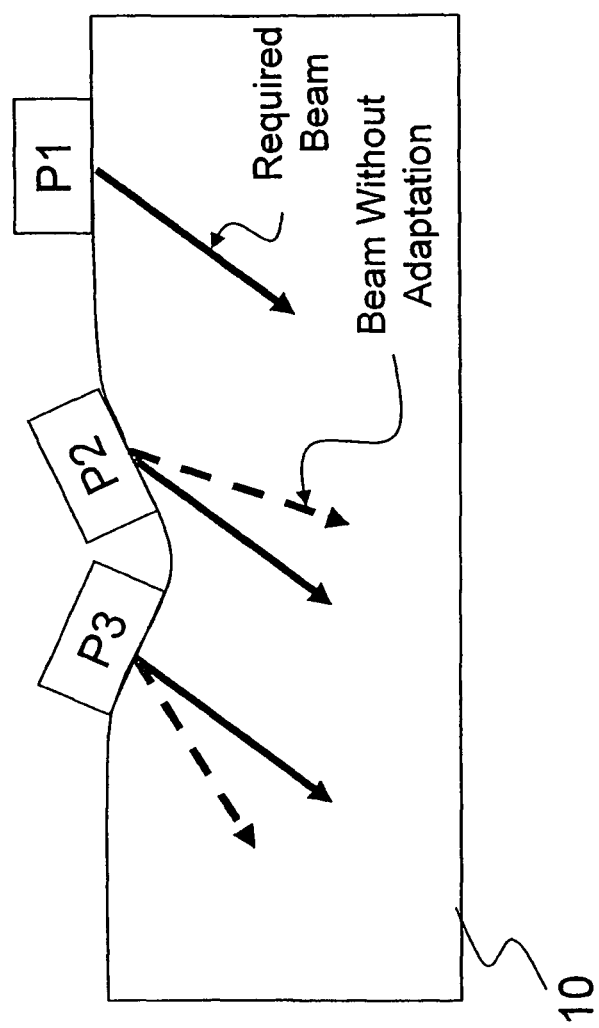
FIG. 2 is a schematic showing a probe inspecting a surface with complex geometry.

In general terms, it has been recognized that in phased array ultrasonic testing, when a specimen has a complex geometry requiring the adaptation of focal laws, a computer model, such as a computer-aided-design (CAD) model, of the specimen can be used to partition the specimen into distinct geometric regions and a set of focal laws can be developed for each region prior to inspection. Then, during inspection, as the probe moves from one geometric region to another, the associated set of focal laws for each region is simply retrieved from memory. This has the advantage of reducing the inspection time since new focal laws do not need to be calculated during inspection. It also allows the designated regions and associated focal laws to be re-used during multiple scans of the same object (or another object with the same geometry) since focal laws are not being calculated on the fly during the inspection process.

Additionally, as will be explained, a method of compressing an A-scan has also been developed using a windowing technique. Methods for computing and displaying volumetric slices in real-time, and for increasing the inspection time in multi-probe systems have also been developed.

Turning now to FIGS. 1-A and 1-B, there is shown a schematic of a system for performing ultrasonic testing. A scanner comprising a single probe 12, such as a phased-array probe, is applied to the specimen 10 to be inspected. The probe 12 is connected to a computing device 14, which comprises hardware and software for performing ultrasonic testing and analyzing and/or displaying the results. The device 14 will typically include a processor 16, a memory cache 18, an internal or external memory disk drive 20, a display 22, inputs and outputs, and various computer subsystems or dedicated modules 24 having computer executable instructions stored thereon for executing the analysis of data. It will be appreciated that FIG. 1-B represents only a generalized schematic of device 14 and that software and hardware for performing the operations described in detail below may be configured in a variety of ways. Typically, device 14 commonly comprises a computer with dedicated software, which connects to an inspection instrument housing the probe(s). The inspection instrument and computer are often packaged as separate units, but this need not be the case.

As inspection progresses, the probe 12 is moved along the surface of specimen 10. As shown in FIG. 2, when the probe moves into a different geometric region (e.g. from position P1 to position P2), it is desired to adapt the focal laws in order to maintain the accuracy of the inspection. For example, if the probe is performing an azimuthal scan at an initial particular angle of refraction, as the surface geometry of the specimen 10 changes, the set of focal laws would need to be adapted to maintain a constant focus area.

Figure 3:
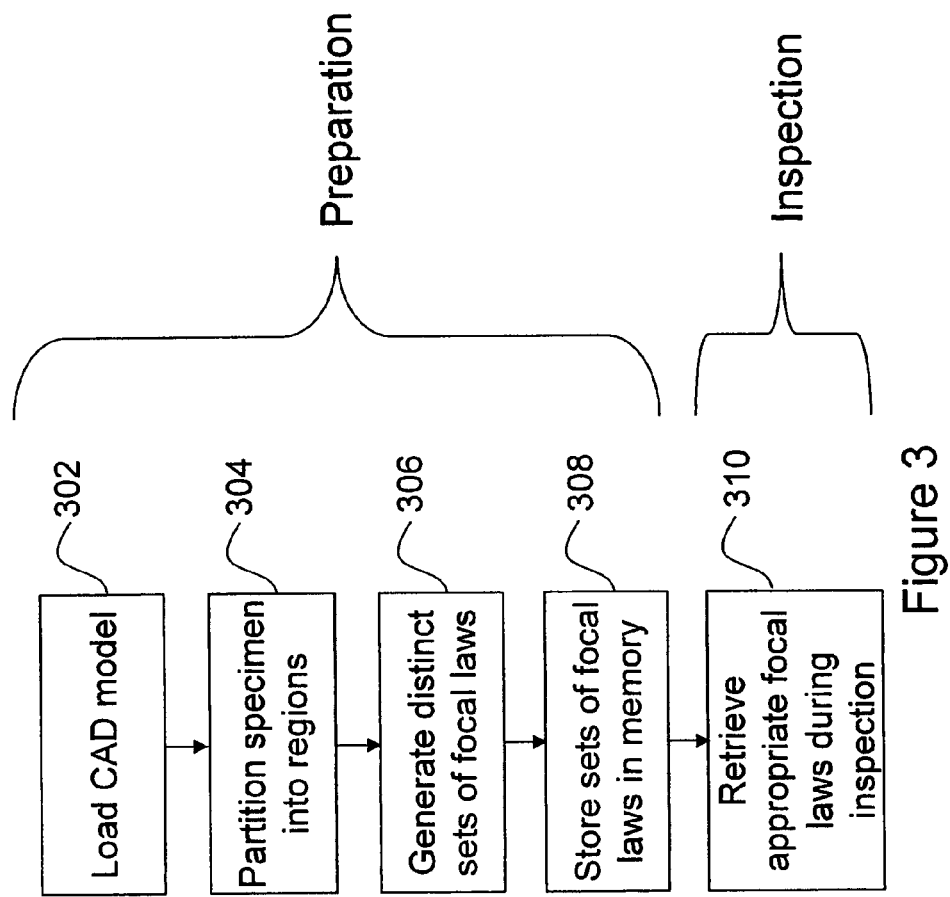
FIG. 3 is a schematic diagram of a set of computer executable instructions for an embodiment of a method of inspecting a specimen.

An embodiment of a method of establishing position dependent focal laws and dynamically accessing these focal laws during inspection is shown in FIG. 3. In this figure, a set of computer readable instructions is shown that are stored in module 24a. Prior to inspection, in step 302, module 24a in device 14 responsible for adapting the focal laws loads into its memory (not shown) a CAD model of the specimen 10 to be inspected, if available. If an accurate CAD model is not available, it is acquired using module 24b, as will be explained in further detail below. In step 304, after acquiring the CAD model, the model of specimen 10 is partitioned into discrete regions, with each region defining a part of the specimen with distinct geometric properties from the other regions. As will also be explained in detail below, the partitioning is done in a way that minimizes the global error, while at the same time maintaining the number of regions (i.e. the number of sets of focal laws) below or equal to a set maximum. Once the CAD model has been partitioned into discrete regions, in step 306 a distinct set of focal laws is generated for each region. In step 308, the discrete regions, as well as each associated distinct set of focal laws, are then stored in memory to be retrieved and utilized during actual inspection of specimen 10. During inspection of specimen 10, in step 310, the position of the probe 12 is monitored, and the associated set of focal laws is retrieved and utilized whenever the probe 12 enters a new region.

In the above described method, by partitioning the regions and calculating distinct focal laws for each region prior to inspection, the actual inspection time is kept to a minimum since updated focal laws do not have to be calculated during scanning. The software in device 14 simply monitors the position of probe 12 and applies the appropriate set of predetermined focal laws. This is particularly advantageous if inspection time is critical, for example, if the specimen 10 is unable to perform its dedicated function during inspection.

Figure 4:
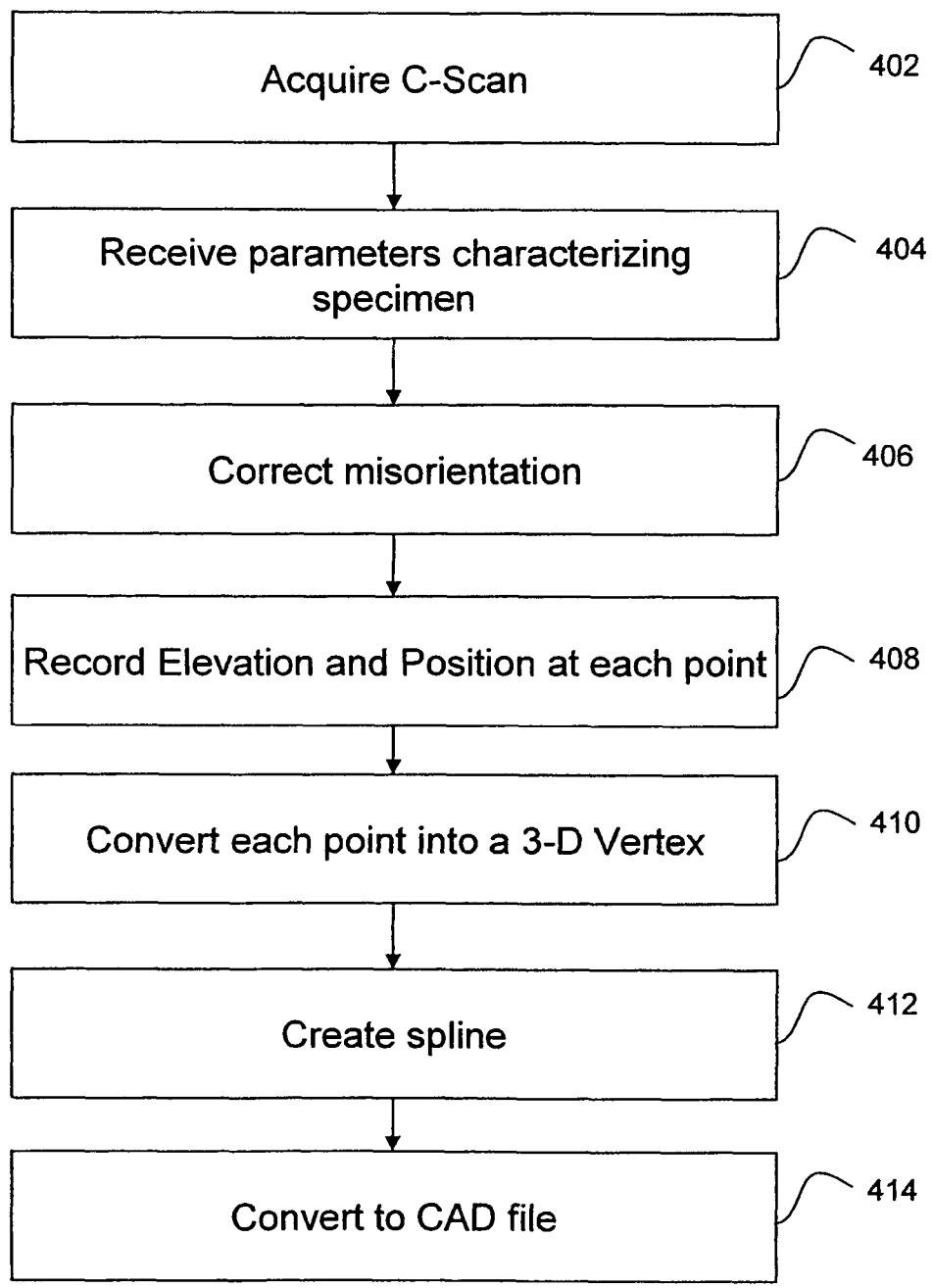
FIG. 4 is a schematic diagram of a set of computer executable instructions for an embodiment of a method of generating a CAD file from a position C-Scan.

The method described in FIG. 3 utilizes a CAD model, and therefore it will be appreciated that an accurate CAD model of specimen 10 is required. However, the CAD model for a specimen is not always readily available, for example, if the blue print is lost, not accurate, or not in a format able to be translated into a CAD file. FIGS. 4 and 5 respectively disclose a method of obtaining a CAD file from a position C-scan of the interface and from an image file of a surface profile transcribed using a manual profiling tool.

Turning first to FIG. 4, an embodiment of a method is disclosed for obtaining a CAD file from a position C-scan of the surface. C-scans are well known in the art and comprise a two-dimensional matrix of data in which each point represents the depth of the discontinuity (in this case the surface) at a given physical position. In this figure, a set of computer readable instructions is shown that are stored in module 24b.

In step 402, the module 24b in device 14 responsible for generating CAD models receives a request to generate a CAD model from a position C-Scan. The C-Scan comprises a set of values with each value representing a position on the surface of the specimen and an associated height measurement representing the relative elevation at that position on the surface. The C-Scan is loaded into memory in module 24b. In step 404, parameters characterizing the specimen represented by the C-Scan are provided to module 24b, typically by a user through a user interface. Such parameters typically include the length and width of the specimen, the thickness of the specimen, and the type of specimen (e.g. the C-Scan may represent a plate, or it may represent the inner or outer surface of a pipe, in which case a diameter parameter would usually also be provided to module 24b). These parameters are used in generating the CAD file. In step 406, the user also corrects for incorrect orientation of the C-scan in comparison to the actual orientation, if necessary. This would occur, for example, if the x-y-z axes of the scanner as positioned above the specimen are slightly deviated or offset in relation to the actual orientation of the specimen. Correction may be done, for example, through a user-interface such as a GUI. For example, the user may first define the boundaries of the C-Scan to be converted into a CAD file, and then correct each x-y, y-z, and x-z orientation using user-defined reference markers representative of the correct orientation of each plane.

In step 408, each point within the boundaries of the C-Scan to be converted to a CAD file is then visited and the elevation height data and position is recorded. If necessary, the position-height pair is corrected using the orientation correction data received from the user. In this case, preferably the angle of misorientation is used in defining increments along and x and y axes of the C-Scan. For example, using the angle of misorientation, $\theta$, the increments needed to parse a line of data are defined by $\cos \theta$ in the x direction and $\sin \theta$ in the y direction. For parsing a column of data, the increments in the x direction are defined by $\sin \theta$, and the increments in the y direction are defined by $\cos \theta$.

Next, in step 410, each corrected position-height is converted from its representation in a C-Scan to representation as a 3-D vertex. Typically, the C-Scan representation is a two dimensional matrix representing the x-y position of the specimen in one dimension, and the height associated with each x-y position in the other dimension. The conversion could be as simple as representing each x-y position and height as an x-y-z coordinate where x and y represent the x-y position on the C-Scan, and z represents the height.

Preferably next, in step 412, a spline is constructed such that the scanned surface can be represented using an equation. Whilst not necessary for generating a CAD model, creating a spline reduces the memory footprint and makes future operations involving the surface more efficient. It will be appreciated that the spline may not be as accurate as a representation using the set of vertices themselves, and therefore it may not always be desired to create a spline.

Finally, in step 414, the set of 3D vertices, or the spline if generated, is converted into a CAD file using standard commercial software. For example, ACIS™ developed by Spatial Corporation may be used, which allows the creation of CAD files from arrays of points or parametric equations. Other third party software may also be utilized, if desired, to provide advanced visual functionalities (e.g. rotating, translating, zooming, etc. of the CAD model).

In an exemplary embodiment, the method of FIG. 4 also performs interpolations between gaps in the C-Scan and provides noise reduction. Noise or gaps in the C-Scan may occur, for example, if the scanner temporarily fails or is disrupted during scanning or if the area of interest was not fully and properly covered in the scan. For a given x-y position on the C-Scan, the associated height measurement will either be height data or a special code specifying no height data was collected for that position. During the method of FIG. 4, whenever a position with a special code is reached, an interpolation algorithm may be applied to interpolate the missing height value. Interpolation algorithms are known in the art, and the interpolation applied may be relatively complex or may be as simple as taking the average height between neighbouring points.

Noise reduction is also preferably performed by the method of FIG. 4, if requested by the user. For example, a simple noise reduction algorithm that requires relatively little computational power is one that provides a smoothing of all heights using a 3 points average (i.e. summing three neighbouring values and dividing by three); however, a variety of noise reduction algorithms known in the art may be applied.

Turning next to FIG. 5-A, an embodiment of a method is disclosed for obtaining a CAD file from a scanned image file of a profile generated using a manual profiling tool. In this figure, a set of computer readable instructions is shown that are stored in module 24b.

Manual profiling tools are manual instruments used to "memorize" the shape of a surface they are placed upon. Such tools are well known in the art. As an example, FIG. 5-B shows a manual profiling tool 502 that has memorized the shape of a sloped surface (not shown). The tool 502 was placed perpendicular to the sloped surface such that the edge 504 formed the shape of the surface. A pencil trace 506 of the surface has been made by following along the edge 504 of the profiling tool 502. The user would scan the pencil trace 506 into an image file and import or provide the image file to device 14.

As shown in step 510 of FIG. 5-A, the module 24b in device 14 responsible for generating CAD models receives a request to generate a CAD model from an image file of a pencil trace made from a manual profiling tool. The image is loaded into memory in module 24b. It will be appreciated that the image may be in any suitable format, such as in .jpg or .bmp. In step 512, information is loaded into module 24b defining boundaries and defining corrections of any misorientation of the image. Such information is preferably provided by the user via a user-interface such as a GUI. For example, in an exemplary embodiment, the user interacts with a GUI to first mark on the image an indication of the start and end positions of the scanned pencil trace to process. The user then marks a height reference, for example, indicating the highest point on the trace (which would correspond to the highest elevation on the surface) and setting that as the reference point from which elevation is measured. In step 514, parameters characterizing the specimen represented by the manual trace are provided to module 24b, typically by a user through a user interface. Such parameters typically include the length and width of the specimen, the thickness of the specimen, and the type of specimen (e.g. plate, inner or outer surface of a pipe, etc.). These parameters are used in generating the CAD file. In step 516, an "orientation segment" is then generated, i.e., a line at the elevation of the height reference that runs along the x-axis above the pencil trace. In step 518, the orientation segment, and the corresponding pencil trace below the orientation segment, are then parsed into discrete sections from the start of the segment to the end of the segment using a fixed increment. Each parsed section is therefore associated with a position along the trace between the start position and the end position.

Next, in step 520, the elevation of the pencil traced surface below each parsed section of the orientation segment is determined. This comprises the following sub-steps for each parsed section. First, in step 520a, a line is generated perpendicular to the orientation segment along the axis of elevation and in a direction towards the pencil trace. This line intersects the pencil trace at a given distance below the reference height. The measured distance between the orientation segment and the point of intersection corresponds to the elevation of the surface relative to the highest point on the surface. In step 520b, beginning at the orientation segment and moving down the perpendicular line, at each position along the perpendicular line it is determined whether or not there is a pixel above a designated opaqueness threshold. In other words, the software moves along the perpendicular line and looks for the spot where the line intersects the pencil trace, which will occur when the line intersects an opaque pixel. It will be appreciated that the threshold for determining how opaque the pixel must be to qualify as the pencil trace should be set high enough to accommodate dust and other artefacts that may be present and scanned into the image. The threshold should also be set high enough to accommodate pencil traces made on technical drawing paper. Such drawing paper may, for example, have light blue grids or other coloured tinting. In such cases, the pixels of the scanned drawing paper should not be interpreted as being part of the pencil trace. Also, in a preferred embodiment, red markings on the scanned image are also ignored. This is to allow users to provide comments in red on the drawing (e.g. for annotations etc.). In step 520c, once the pencil trace is identified, the distance between the orientation segment (which is at the elevation of the reference height) and the pencil trace is measured. The elevation of the reference height, as well as the distance of the pencil trace below that elevation is used to calculate the elevation of that parsed section of the pencil traced surface. Steps 520a to 520c are repeated for each of the parsed sections along the orientation segment.

In an exemplary embodiment, the method of FIG. 5-A also provides interpolation between gaps in the pencil trace. Such gaps may occur, for example, if the pencil trace is faded in sections (and therefore not opaque enough to be identified in step 520b). In this case, during step 520b, if no pencil trace pixel is identified, then interpolation is performed to estimate the location of the trace using the elevation of neighbouring parsed sections of the trace. Interpolation algorithms are known in the art, and the interpolation applied may be as simple as taking the average height between neighbouring sections.

After the elevation or height of each section of the pencil trace has been calculated, in step 522 each position-height pair calculated during step 520 is corrected using orientation correction data received from the user, if necessary. Preferably, the orientation correction data is provided by the user using a GUI. For example, the user could draw a reference marker defining the correct line of orientation. Next, in step 524, each position-height pair is represented as a 3-D vertex.

The steps for generating the CAD model from this point are the same as the final steps for generating a CAD model from the position C-Scan. That is, in step 526, a spline is preferably constructed, and in step 528, the set of 3D vertices, or the spline if generated, is converted into a CAD file using standard commercial software.

In summary, FIGS. 4 and 5-A have disclosed embodiments of methods for generating a CAD model from a position C-Scan and a manual trace respectfully. It will be appreciated by a person skilled in the art that some steps in FIGS. 4 and 5-A may be interchanged without affecting the performance, intent, or consequence of the method. As an example, steps 512 and 514 in FIG. 5-A could be interchanged with no affect to the rest of the method.

Partitioning Method

Returning now to FIG. 3, as explained in step 304, the CAD model of specimen 10 is partitioned into discrete regions, with each region defining a part of the specimen 10 with distinct geometric properties from the other regions. In general, a change in geometry of an actual specimen is often not marked by a discrete change at a given location. Instead, the change in geometry is often progressive, and in such a case the geometry is not exactly the same for two different positions of the probe. This presents a challenge since the CAD model can only be partitioned into a maximum number of geometric regions, usually limited by the number of focal laws supported by the equipment.

Figure 6:
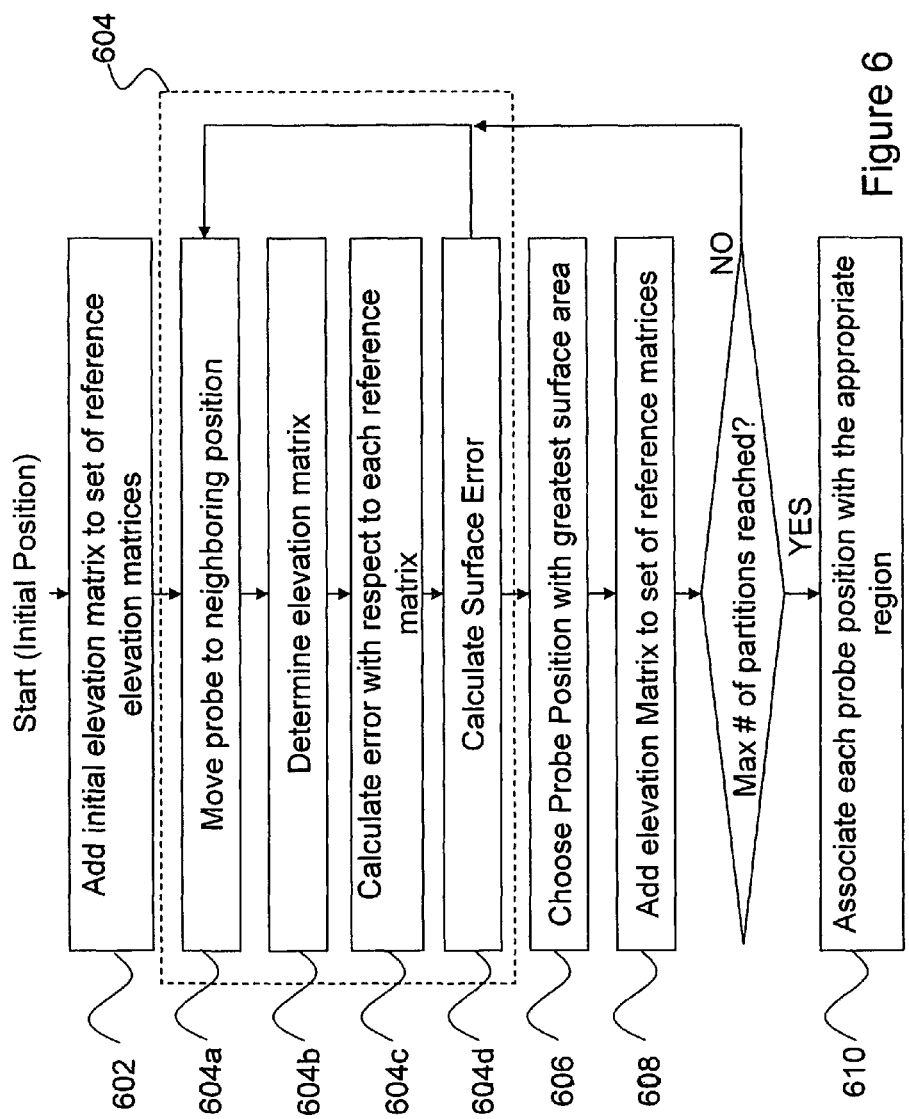
FIG. 6 is a schematic diagram of a set of computer executable instructions for an embodiment of a method of partitioning a CAD file.

FIG. 6 outlines an embodiment of a method performed by module 24c for partitioning a CAD model into distinct geometric regions in a way that seeks to minimize (or if possible eliminate) the error introduced when partitioning a progressively changing surface into a discrete number of distinct geometric regions. In this figure, a set of computer readable instructions is shown that are stored in module 24c.

One important input parameter to such an algorithm is the maximum number of distinct geometric regions. This maximum may be derived using the number of sets of focal laws that the equipment can support and/or the maximum total number of focal laws the equipment can support. Another important input parameter to the algorithm is an initial set of focal laws.

Preferably, the set of focal laws defines the "probe shadow" of the probe, i.e., the area covered by the steering sequence of the beam. The area defined by the probe shadow at each probe position is represented using a data structure, preferably a matrix of points spanning the area. For a given probe position (i.e., a given region on the CAD drawing), each point in the matrix spanning the probe shadow is a number that represents the elevation of the surface at that point. In other words, at each probe position (i.e. in each region on the CAD drawing), the associated probe shadow will be represented by a dedicated matrix of points capturing the elevation of the surface within the shadow. This is referred to as the elevation matrix. As the surface changes, the values in the elevation matrix representing the probe shadow will change to reflect any change in elevation. In this way, the elevation matrix is an example of a data structure that characterizes the surface associated with the probe position. Specifically, it characterizes the elevation of the surface within the probe shadow.

It will be appreciated that the more points in the elevation matrix (i.e. the higher the resolution), the more accurate the characterization of the surface will be. Therefore, a higher resolution matrix will result in better performance of the overall partitioning process. However, higher resolution also requires more memory and computational power. A preferred resolution is a matrix ranging in size between 4×4 (16 points) and 16×16 (256 points), but matrices of larger or smaller dimensions are possible.

It will also be appreciated that the probe shadow need not necessarily be limited to the actual area defined by the set of focal laws. In the preferred embodiment, the probe shadow is set as the area defined by the focal laws expanded by 10% in all directions. Areas of other sizes are also permitted without affecting the fundamental operation of the partitioning method.

Additionally, in alternative embodiments, other methods of defining the probe shadow are contemplated. For example, in an alternative embodiment, the probe shadow may not be defined only by the set of focal laws, but instead or also from the physical size of the probe. Regardless, the resulting area covered by the probe shadow is still represented by an elevation matrix, and it will be clear to a person skilled in the art that how the probe shadow is defined does not affect the fundamental operation of the partitioning method described in FIG. 6.

Turning first to step 602, the partitioning algorithm initially assumes a single geometric region defined by the region under the initial probe position. The associated elevation matrix, which characterizes the surface of the initial probe position, is stored as a reference elevation matrix. As will be explained in more detail below, reference elevation matrices are used for calculating error with respect to regions, and once additional geometric regions are defined, a reference elevation matrix will be stored for each region.

For every other probe position, the elevation matrix is then determined for the probe shadow and the "surface error" is calculated. This is shown in step 604. The surface error for a given probe position is defined as the minimum error value in the set of errors calculated between the given probe position and each reference elevation matrix. For a probe position with elevation matrix A, and for a given reference elevation matrix B, the error between A and B is preferably defined by the root mean square error of the difference between each matrix point:

$$\text{error} = \sqrt{\frac{1}{n}\sum_{i,j}(a_{ij} - b_{ij})^2},$$

where $a_{ij}$ and $b_{ij}$ represent points in each respective matrix and n represents the size of each reference elevation matrix. This is an example of a measure of difference between surface characteristics represented by elevation matrices A and B respectively.

Assuming the above equation for measuring error, the surface error for a given probe position is preferably calculated as:

$$\text{surface error} = \min_{\text{over all } B}\left(\sqrt{\frac{1}{n}\sum_{i,j}(a_{ij} - b_{ij})^2}\right).$$

Initially, there will only be one reference elevation matrix, which corresponds to the initial position of the probe. However, as additional geometric regions are defined (steps 606 to 610), each new geometric region will have an associated reference elevation matrix. Although for a given probe position the error may be large with respect to one reference elevation matrix (i.e., there may be a large difference in the geometric properties of the surface), with respect to another reference elevation matrix, the error may be negligible (i.e., the geometric properties of the surface may be almost identical). This is why the surface error is defined as the minimum of the errors: in the latter situation, there would be no need to define a new geometric region for the current probe position because it is almost identical to one that already exists.

In step 606, once the surface error for each probe position is calculated, the probe position with the largest surface error is identified. This is the probe position that benefits most by being associated with a new geometric region (and hence an associated new set of focal laws). This probe position is then designated a new geometric region, and its elevation matrix is added to the set of reference elevation matrices (step 608). Assuming the maximum number of possible regions has not been reached, the algorithm begins another iteration by returning to step 604. In this way, an additional geometric region is defined with each iteration, and with the creation of each additional geometric region, the overall error for each probe position can be reduced.

Once the maximum number of allowed regions has been reached, in step 610 each probe position is then associated with the geometric region to which it has the closest geometric properties (so that during step 310 of FIG. 3 the best set of focal laws are utilized for each position of the probe). This association is stored in memory. Step 610 can be achieved, for example, by calculating the surface error for each probe position using the complete set of reference elevation matrices. If desired, a C-Scan could be created linking each position of the probe to the proper partitioned region. Such a C-Scan could be displayed to the user. Finally, each partitioned region is then fed to the focal law calculator in step 306 of FIG. 3 to generate the new set of focal laws for that region.

Preferably, the partitioning method described in FIG. 6 is terminated early if after completing step 604 it is determined that the surface error of all probe positions is substantially zero. Such a scenario could occur if the surface to be inspected did not change progressively, but instead was characterized by a discrete number of distinct geometric regions. Once all regions were captured, the surface error of all probe positions would be zero since each probe position would belong to one of the partitioned geometric regions. There would be no need to create additional geometric regions.

The above method described with reference to FIG. 6 is exemplified in the context of using a scanner comprising a single probe 12. It will be appreciated that the method of FIG. 6 could also be implemented using a scanner with multiple probes (not shown). In such a system, the shadows of all probes would need to be considered in calculating the surface error at each scanner position. For example, consider a scanner having two probes in fixed relation to each other. It may be the case that during step 604, for a given scanner position the first probe may have a very low error with respect to a given reference elevation matrix; however, the second probe may have a high error with respect to that matrix. Because of such scenarios, for multi-probe scanners, the error of each probe would need to be factored into the error calculation for each scanner position. This could be achieved, for example, by simply adding the errors of each probe with respect to each reference elevation matrix. In an alternative embodiment, for every scanner position each probe attached to the scanner could have its own associated surface error and geometric region independent of the other probes. In this case, multiple geometric regions would be associated with each scanner position.

Finally, if desired, the partitioning method described in FIG. 6 may also include calculating the maximum error of each region, as well as the average error, and displaying such values to the user. For example, once the steps of FIG. 6 are complete, the maximum error may be calculated as the scanner position that has the largest surface error, and the average area may be calculated the average of the surface errors.

A-Scan Compression

Regardless of whether the inspection of the specimen 10 is performed using the method described in FIG. 3, or whether a simple conventional ultrasonic scan is being performed, the fundamental data retrieved after each ultrasonic beam is fired into the specimen 10 is an echo, which is commonly captured in an A-scan. As discussed earlier, an A-scan is a vector that records the amplitude of the echo at each measured time unit. The length of the vector is equal to the number of measured time units. Therefore, each vector position represents a position in time with each position having an associated amplitude value.

Figure 7:
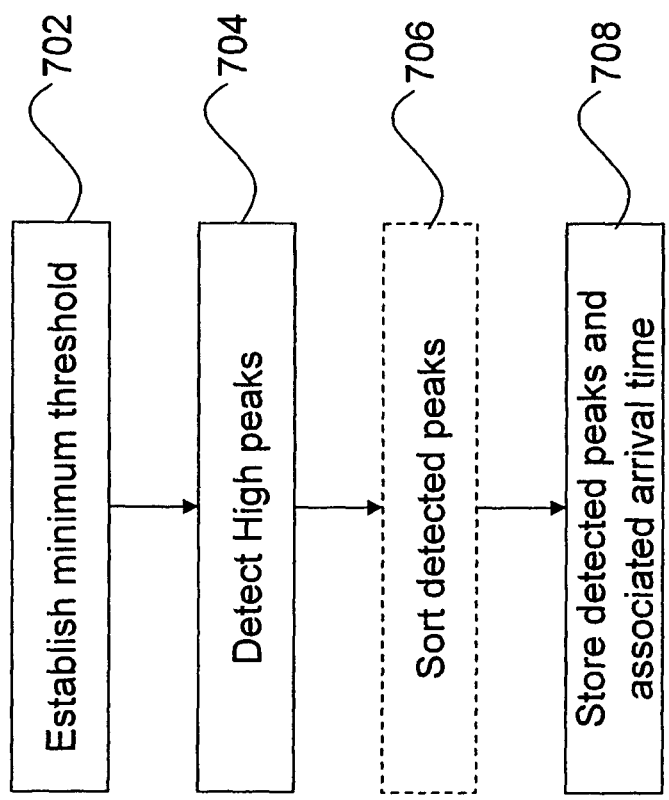
FIG. 7 is a schematic diagram of a set of computer executable instructions for an embodiment of a method of compressing an A-Scan.

As described earlier, it is often desired to compress an A-scan in order to reduce storage requirements and to reduce the number of computations required in subsequent processing of the A-scan. FIG. 7 discloses an embodiment of a method for representing an A-scan in compressed form. In this figure, a set of computer readable instructions is shown that are stored in module 24d.

In general terms, the method of compression described in FIG. 7 operates by using a windowing technique to capture and store only the high peaks in the A-scan, along with their associated times of arrival. The resulting compressed A-scan requires substantially less storage space since all data in the A-scan that does not represent a high peak is discarded; however, the compressed A-scan still captures all high peaks and retains a record of where they occurred. This is often the most important or only data required for subsequent processing and interpretation.

Turning to FIG. 7, in step 702, module 24d in device 14 responsible for A-scan compression first establishes a minimum amplitude threshold that must be exceed by the amplitude data in the A-scan before the algorithm searches for peaks. This is to accommodate noise and other small disturbances that may be picked up by the receiver when receiving the return echo. The minimum threshold may be pre-programmed in device 14 or may be set by the user. Also, the threshold may vary over the A-scan if desired.

In step 704, the A-scan is analysed using a windowing technique and the high peaks in the A-scan are detected. Preferably, at this time, each high peak is stored in a new dedicated vector. The arrival time associated with each detected peak is also stored. The remaining data in the A-scan is then discarded. Step 704 will be explained in more detail below.

Preferably (although not necessary), in step 706, the peaks captured in step 704 are then sorted, for example, from highest amplitude to lowest amplitude. Finally, in step 708, each detected peak, and its associated arrival time, is then stored in a new dedicated vector (if not done during step 704). This vector will be substantially smaller than the original A-scan since all amplitude data in the original A-scan not representing the high peaks is eliminated.

Figure 8:
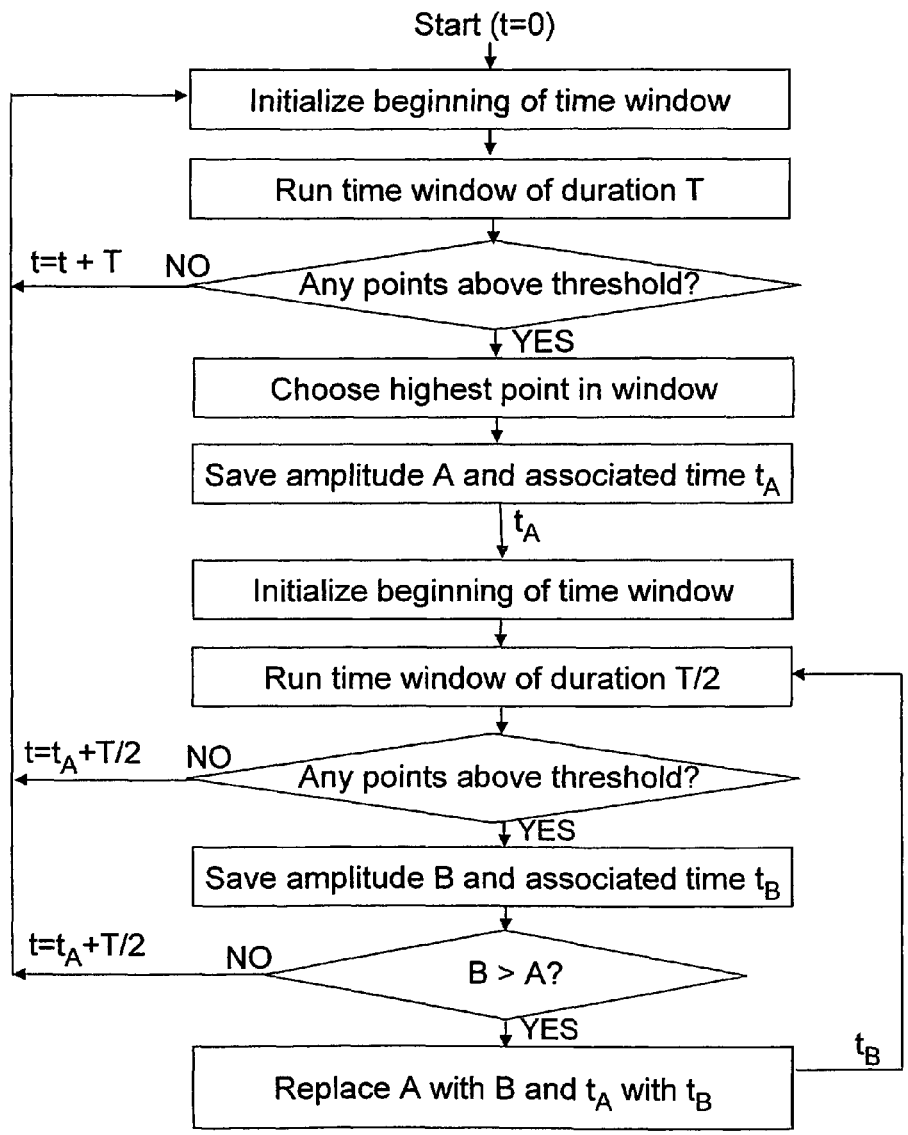
FIG. 8 discloses a detailed embodiment of one method for compressing an A-Scan.

An embodiment of the windowing technique used in step 704 of FIG. 7 to capture the high peaks will now be described with reference to FIGS. 8 and 9. FIG. 8 provides an overview of an embodiment of the windowing technique used in step 704. By way of example only, and with the purpose of better explaining and illustrating the windowing technique described in FIG. 8, an example is shown in FIG. 9 in which the windowing technique described in FIG. 8 is applied to an A-scan having three high peaks.

Figure 9:
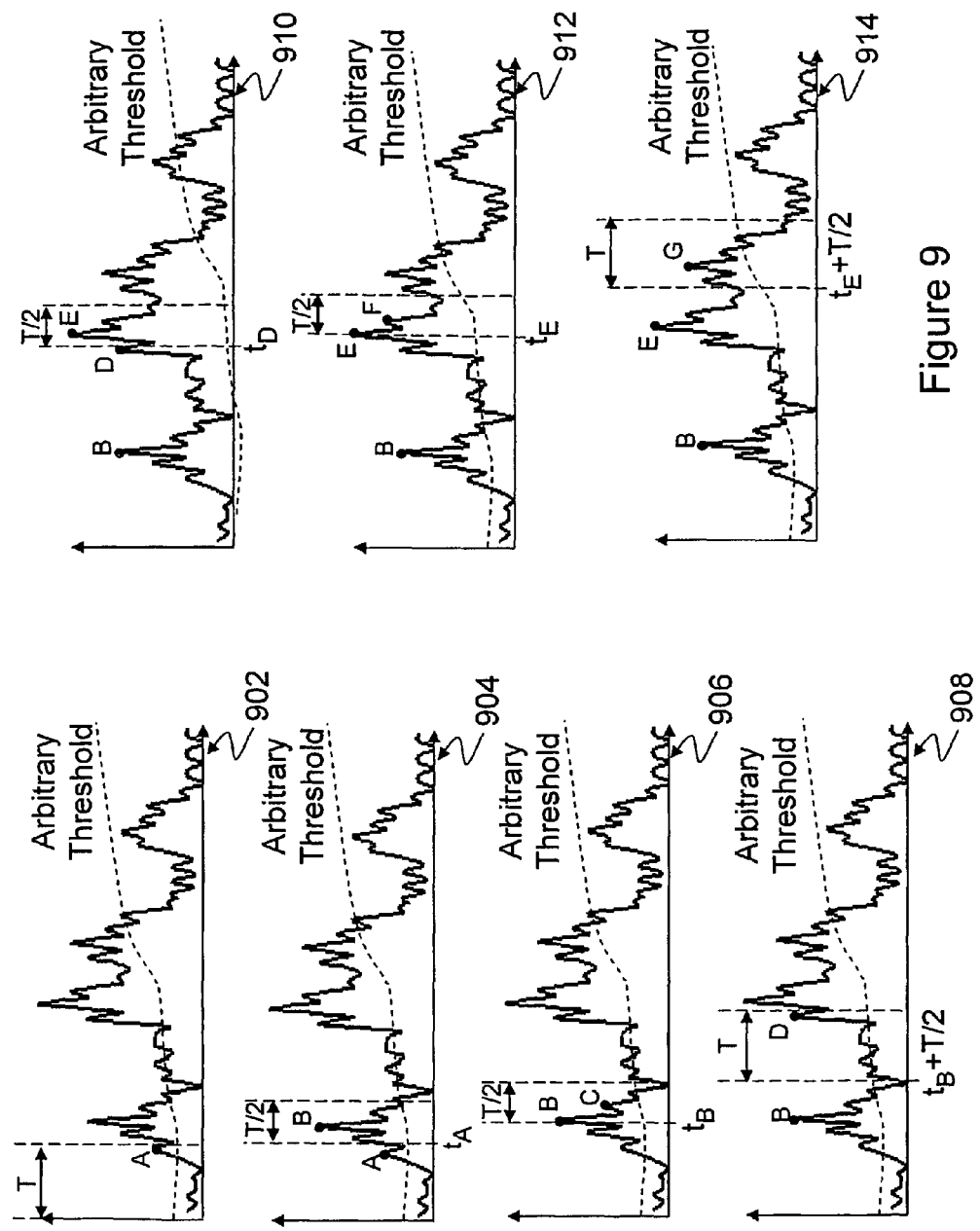
FIG. 9 is an example of the steps of FIG. 8 applied to one particular A-Scan.

Considering the example in FIG. 9, at step 902, once the A-scan data is available, the A-scan is read for a duration of time T. During this time window of duration T, any amplitude data in the A-scan that exceeds the minimum amplitude threshold is recorded. At the end of time window T, if there is no amplitude data that exceeds the minimum threshold (i.e. there are no peaks), then the next block of A-scan data is read for time T. On the other hand, if there is amplitude data in time window T that exceeds the minimum threshold (as in the example in step 902), this amplitude data is compared, and the value of the highest amplitude in the window, along with its associated arrival time, is stored in memory. In this example, the point A has the highest amplitude in the time window T. Therefore, the amplitude of A and its associated arrival time $t_A$ are stored in memory.

Although point A may be the highest peak in the window of duration T, it is not necessarily considered a "high" peak. Point A may instead be a "lead-up" peak adjacent to or neighbouring the local high peak. In such a scenario, it is this adjacent higher peak that should be captured since this is the peak that best characterizes the discontinuity that caused the echo. Therefore, in step 904, beginning from time $t_A$, the A-scan is read for a shorter duration, for example for a duration of time T/2. During this shorter time window, the peak with the highest amplitude is recorded (point B in step 904) and is compared to the amplitude of the highest peak in the previous window (point A). If the amplitude of B is greater than the amplitude of A, A is discarded and B is stored in memory. Such is the case in step 904. Otherwise, if point B does not have an amplitude greater than point A, point A is considered to be the local high peak and is transferred to a new dedicated vector for storing the compressed A-scan. In this case, the process would then repeat using a new time window of duration T beginning at time $t_A$+T/2.

In step 904, point B is found to have a higher amplitude than point A. Therefore, point A is discarded from memory and point B is instead stored. However, point B may also be a "lead-up" peak adjacent to or neighbouring the local high peak. Therefore, in step 906, beginning from time $t_B$, the A-scan is again read for a duration of time T/2. During this time window, the peak with the highest amplitude is recorded (point C in step 906) and compared to the amplitude of the highest peak in the previous window (point B). If the amplitude of C is greater than the amplitude of B, B is discarded and C is stored in memory. In the example in FIG. 9, the amplitude of point C is less than the amplitude of point B, and therefore point B is retained. Point B is the local high peak. It is therefore transferred to the new dedicated vector for storing the compressed A-scan.

The process continues in steps 908 to 914. In step 908, the point D is determined to be the highest peak in time window T. However, it is replaced by point E in step 910. In step 912, point F is considered, but is not retained since it does not have an amplitude greater than point E. In step 914, point G is determined to be the highest peak in time window T. Subsequent peaks (e.g. point H) are not considered because they are below the minimum threshold.

Therefore, in the A-scan of FIG. 9, three high points (B, E, and G) are isolated and stored in the new dedicated vector for storing the compressed A-scan. Their associated arrival times ($t_B$, $t_E$, and $t_G$) are also stored in the vector. Advantageously, this vector is much smaller than the original A-scan. As shown in step 706 of FIG. 7, these three points may be sorted in order of increasing or decreasing amplitude.

It will be appreciated that the time windows used in the above-described windowing technique may be of different durations and may be either pre-programmed or input by a user. For example, the duration of the shorter time-window (T/2) need not be half of the duration of the longer time window (T). In fact, the optimum duration of each time window will depend on the expected characteristics of the A-scan.

The compression technique described in FIG. 7 allows for compression of the A-scan while still capturing the amplitudes and times of the high peaks. This compression technique is particularly advantageous because it is computationally simple enough to be effectively employed in real-time, i.e., as the echo from a given beam is being received and the A-scan is being formed.

Volumetric Slicing and Caching

Figure 10:
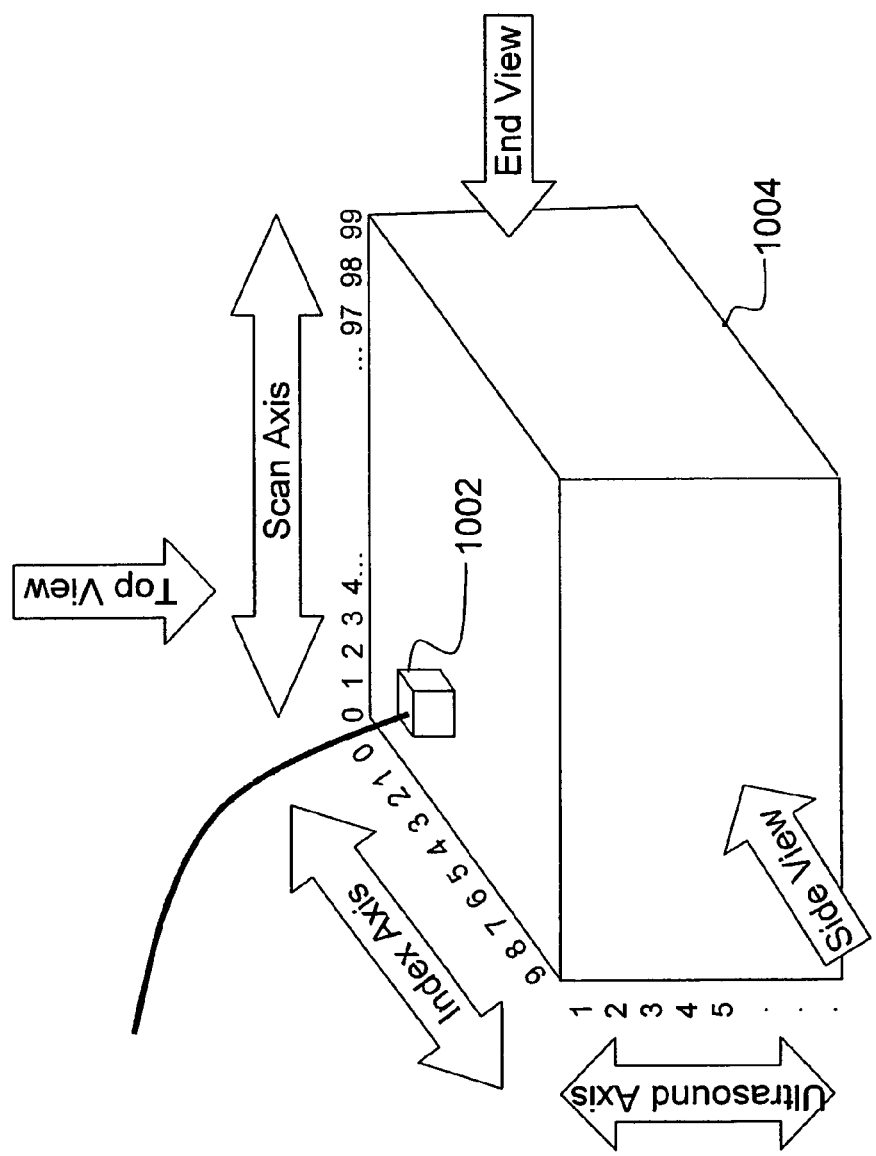
FIG. 10 is a schematic of a probe scanning a specimen.

During the scanning of a specimen, often a large amount of data is collected and stored in memory for post-scanning analysis by device 14. This data may be manipulated and stored as volume data, thereby allowing a user to view 3-D images and/or 2-D volumetric views of the specimen. For example, the data acquired during scanning may be represented using a data structure such as three dimensional matrix in which two dimensions are associated with the physical position of the scanner on the surface of the specimen and the third dimension represents the depth and characteristics of the flaw or discontinuity in the specimen. Consider, as a simple example, FIG. 10, which shows a single probe 1002 scanning a specimen 1004. The probe 1002 scans the specimen 1004 by moving up and down the "scan" axis and along the "index" axis, starting at position [0,0] and finishing at position [99,9]. At each position, the probe 1002 fires into specimen 1004 to collect data that characterizes the depth and shape of any discontinuities in specimen 1004, such as from a crack. For simplicity, assume at each probe position, a single A-scan is obtained. The length of the A-scan vector represents the number of measured time units, which corresponds to the depth within the specimen (shown by the "ultrasound" axis in FIG. 10). The magnitude of the A-scan vector at each sample point along the ultrasound axis represents the magnitude of the returned echo associated with that depth. In this way, it can be seen that the volume of the specimen 1004 can be represented as a three dimensional matrix with each matrix entry corresponding to a point on the scan-index-ultrasound axes. Each matrix entry represents the magnitude of the amplitude at that physical position. The number of bits representing each matrix entry will vary depending on the implementation, but may be, for example, between 8 and 32 bits. Such three dimensional representations of volume data are known in the art.

It will be appreciated that the three dimensional representation of volume data may be constructed from means other than A-scan data. For example, the volume matrix may instead be constructed using a C-Scan of the specimen. In this case, for each scan-index position, there would only be a single amplitude position at a specific depth along the ultrasound axis. The rest of the positions along the ultrasound axis would be zero. Alternatively, the matrix may be constructed from compressed A-Scan data, for example, A-scans compressed as described in the present application. In this case, for each scan-index position, the ultrasound axis would be populated with the peak amplitude(s) captured in the associated compressed A-Scan. Other positions along the ultrasound axis (between peaks) would be set to zero.

Upon completion of the scanning, and after the volume data is computed and stored, the user will often interact with system 14 to access two-dimensional volumetric views or "slices" of the volume data from different perspectives to search for flaws in the specimen. A slice is generally defined as three dimensional volume data projected on a two dimensional plane. For example, consider viewing the volume data representing specimen 1004 from the top (i.e. a "top view"). The slice viewed by the user would correspond to a two dimensional plane with the scan axis as the x-axis and the index axis as the y-axis. For each scan-index position (i.e. x-y position), a coloured dot, number, or equivalent displayed to the user would provide an indication of the maximum amplitude of the depth data along the ultrasound axis. It is this maximum amplitude that is of interest because it is this depth position that represents substantially the exact point where the discontinuity is located. In the simple example, the slice would be equivalent to a C-Scan. The slice could have instead been taken only between certain defined upper and lower boundary planes, for example, between samples 10 and 100 along the ultrasound axis. In this case, the two dimensional projection would only show the maximum amplitude between samples 10 and 100. Slices may also be created by projecting data on the index axis (i.e. a "side view") or by projecting data on scan axis (i.e. an "end view").

In this way, it can be seen that for a given directional view, a slice is defined as a two dimensional projection of the maximum amplitude of the volume data between any two planes perpendicularly intersecting the axis that runs in the direction of the view. The two planes define the boundaries of the slice and are generally spaced from one another along the axis; however, in general both planes may intersect the axis at the same point, in which case there would only be one amplitude value to project. Creating slices (or the equivalent) is a technique known and employed by those skilled in the art.

It is desired that the user be able to use system 14 to request and view slices between certain locations along either the ultrasound, scan or index axis, in order to be able to better identify and characterize any flaws. For this reason, the system 14 allows the user to define custom slices; i.e., to choose the directional view of interest and define the locations of the two planes intersecting the projected axis, thereby defining both the x-y axis of the two dimensional slice view and the range of the z axis that will be projected in the slice. Creating such custom slices in real-time or near-real-time is a problem when the volume data is large (e.g. several gigabytes). Such a large amount of volume data cannot be stored in quick access memory storage, such as the memory cache 18; rather, the large amount of data must be stored on a larger memory disk 20, which results in a slower slice construction time due to the relatively long access time of disk 20.

Figure 11:
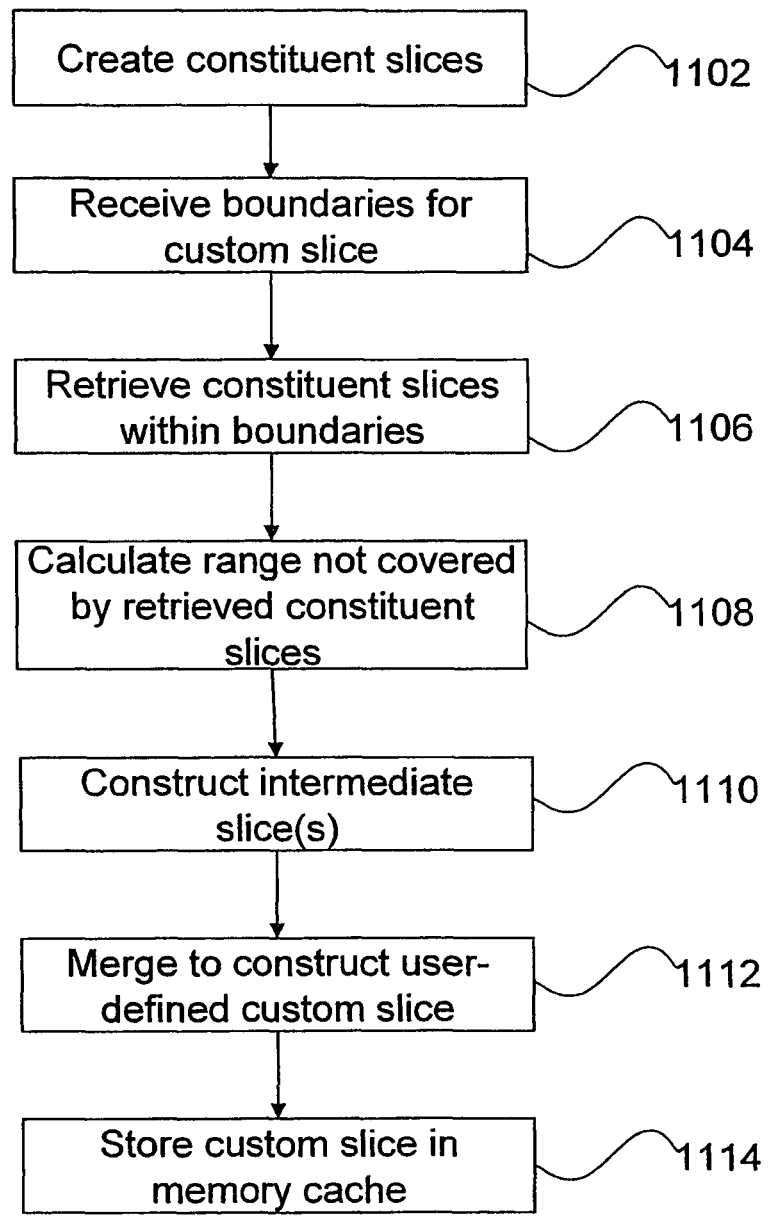
FIG. 11 is a schematic diagram of a set of computer executable instructions for an embodiment of a method of creating user-defined customized two-dimensional views.

It has been recognized that the access speed of the memory disk 20 is a limiting factor when constructing a slice of the volume data, and that therefore it is necessary to reduce or minimize the number of times the memory disk 20 is accessed in order to provide real-time construction of user-requested slices. FIG. 11 discloses an embodiment of one such method. A summary of the method is as follows.

After the volume data has been acquired, but before the user can define custom slices, along each of the scan, index, and ultrasound axes a set of constituent slices is created by module 24e in device 14, responsible for the slicing process. Each constituent slice represents a two dimensional projection of the maximum amplitude data between two sample points along the given axis (i.e., along the given view direction), and the set of constituent slices for a given axis spans the full length of that axis. For example, consider the simple example in FIG. 10, and assume that the projected axis of the slice is the ultrasound axis, and that this axis has 100 sample positions. The number of constituent slices along this axis could be chosen, for example, as ten. In this case, the first constituent slice would span positions 0 to 9, the second would span positions 10 to 19, and so on, up to the tenth constituent slice, which would span positions 90 to 99. In this way, each constituent slice covers one section of the ultrasound axis, and all the constituent slices span the axis. In other words, the axis is partitioned into a set of adjacent constituent slices. A set of constituent slices would also be created for the index axis (side view slices) and for the scan axis (end view slices). Since the constituent slices represent much less data than the three dimensional volume data matrix, most, if not all of the constituent slices could be stored in the memory cache 18.

Subsequently, when the user requests a slice between certain user-designated samples on the projected axis, module 24e chooses the subset of constituent slices that are completely enclosed by the user-designated boundaries. If necessary, one or more intermediate slices are then constructed using volume data on the memory disk 20 for the portion of the user-requested range not covered by the subset of constituent slices. The intermediate slice(s) and subset of constituent slices are then merged to create the user-requested slice. For example, considering again the example of FIG. 10, the user may request a slice that projects the maximum amplitude of the depth data along the ultrasound axis between samples 0 and 24. Module 24e would construct this slice by selecting the first and second constituent slices from the memory cache 18 (spanning samples 0 to 19), and then use the volume data stored in memory drive 20 to create an intermediate slice spanning samples 20 to 24. The first and second constituent slices and intermediate slice would then be merged together to form the custom slice. The merging process will be explained in more detail below.

To explain the above method in more detail, reference is made to FIG. 11. In this figure, a set of computer readable instructions is shown that are stored in module 24e. Turning first to step 1102, module 24e first partitions each directional view of the volume into a set of constituent slices, as described above. The number of samples included in each constituent slice (i.e. the number constituent slices per view) should be chosen to allow efficient construction of user-defined slices, while keeping memory requirements low to preferably enable all constituent slices to be stored in the memory cache 18. In general, a larger set of constituent slices allows for a more efficient creation of user-requested custom slices; however, more constituent slices increases the memory requirements. In an exemplary embodiment, the number of constituent slices for a given view is a function of the number of total samples along the projected axis. For example, in one embodiment, the number of constituent slices for a given projected axis is calculated as follows:

$$\begin{cases} 1, \text{ if } s \leq 10, \text{ else} \\ \sqrt{s}, \end{cases}$$

where s represents the total number of samples along the projected axis. For example, if the number of samples along the projected axis was 100, the number of constituent slices would be 10, with each constituent slice representing one tenth of the total number of samples on the axis.

The constituent slices are stored in the memory cache 18 to be used for constructing user-defined custom slices, as will be explained in the remaining steps in FIG. 11.

In step 1104, a user request is received (e.g. through a user interface of device 14) which defines the boundaries of a custom slice that the user wishes to view along a given directional view (top, side, or end). The range along the projected axis covered by the user-requested custom slice is stored. In step 1106, the constituent slices in the memory cache 18 are searched and the subset of constituent slices are retrieved that fall within the user-requested boundaries (i.e. that are entirely encompassed by the range defined by the user). In step 1108, the remaining range not covered by the subset of constituent slices, which makes up the intermediate portion, is calculated by subtracting from the user-requested boundary range the range covered by the retrieved constituent slices. It will be noted that steps 1104 to 1108 do not require accessing the volume data on the memory disk 20 since the constituent slices are stored in the memory cache 18. This has the effect of substantially reducing the time required to construct a user-requested slice. In step 1110, one or more intermediate slices are then constructed for the intermediate portion. No intermediate slice(s) need be constructed if the user-requested range is fully covered by the subset of constituent slices.

To construct each intermediate slice, volume data on the memory drive 20 is accessed; however, the number of accesses (and hence the total access time) is substantially less than if the user-requested slice is calculated without using the constituent slices stored in the memory cache 18. Finally, in step 1112, the subset of constituent slices and intermediate slices are merged to create the user-requested slice. The merging process is preferably embodied as follows: for each x-y position of the directional view, the amplitudes projected in each of the subset of constituent slices and intermediate slices are compared, and the maximum amplitude value is chosen. As will be appreciated, for each x-y position, the maximum amplitude value of each of the subset of constituent slices and intermediate slices clearly represents the maximum amplitude within the user-selected range at that x-y position.

In summary, module 24e allows device 14 to create user-defined custom slices in a way that minimizes the number of accesses to the volume data stored in memory disk 20. The volume data is only parsed once into constituent slices, and these constituent slices are then stored in the memory cache 18. The only time the slower memory disk 20 needs to be accessed is during the construction of an intermediate slice, and only then for the relatively small portion of data not covered by the constituent slices. It may be noted that if the memory cache 18 is of a very limited size and cannot hold all of the constituent slices, some of the constituent slices may be stored in memory disk 20. Although this is not preferred (since more accesses to the memory disk 20 would be required during the method of FIG. 11), the method described in FIG. 11 would still produce faster custom slice construction than if constituent slices were not used.

In the above discussion, the concept of a "slice" has been discussed with regard to a projection of data in a three dimensional matrix of volume data. The creation of slices, or the equivalent, is known in the art, and it will be appreciated by those skilled in the art that the matrix of volume data, as well as the slices, may be created from a variety of underlying data, for example from a compressed A-Scan(s) or from a C-Scan. In the case of C-Scan data, the creation of a slice could be as simple as a copy from the C-Scan memory to the slice memory. Offsets or corrections to the data comprising the slice may also be applied. In any case, the method of creating constituent and intermediate slices to allow for the fast creation of user-defined custom slices, as described in FIG. 11, remains unchanged.

It has additionally been recognized that a user often requests the same custom slice several times in a single session. For example, it is common for a user to generate new boundaries for a brief period of time and then return to previous settings. Therefore, it is preferable, if possible, for module 24e to maintain recently generated custom slices in the memory cache 18 so that they can be quickly retrieved during a later time in the session. This is shown in step 1114 of FIG. 11.

During operation, for each volume data file, the associated constituent slices is generated as described in step 1102. As discussed above, these constituent slices are stored in the memory cache 18 if possible to allow for quick construction of custom slices. However, often a user will have multiple volume data files related to single specimen or set of specimens. In such a scenario, it is common for the user to use the same file or files multiple times before it is no longer needed. This presents a memory management problem: it is undesirable to regenerate constituent slices each time a volume data file is opened; however, limited memory disk space prevents each volume data file and its associated set of constituent slices from being stored indefinitely. Such a problem can be managed by having a module that monitors when a volume data file was last opened. When the designated memory drive space is full, files that have not been opened recently are deleted.

For example, when a volume data file is first acquired, the constituent slices are generated as described in FIG. 11 and stored in the memory cache 18. As the user requests custom slices, these are also generated as described in FIG. 11, and, if possible, the custom slices are stored in the memory cache 18 also. Once the file is closed by the user, the volume data, as well as its associated constituent slices and recent custom slices generated by the user, are transferred from the memory cache 18 to the memory drive 20 under an associated folder (not shown). A timestamp or the like is associated with the saved file indicating when the file was last opened. When the user wishes to reopen the file, the associated constituent slices and/or custom slices are loaded back into the memory cache 18. Every time the file is reopened and closed, the associated timestamp is updated.

As other volume data files are opened and closed, they are also saved in the memory drive 20 along with their associated timestamps. In the event that the portion of the memory drive 20 designated for storing the files becomes full, the timestamps for each file stored in memory is reviewed, and the file in memory that is the oldest (i.e. was opened least recently) can be deleted.

In this way, recently used files are retained in the memory drive 20, and every time one of the recently used files is reopened, the associated constituent slices and/or custom slices are loaded back into the memory cache 18 so that they do not have to be regenerated again from the volume data. This allows a user to reopen the file and quickly view previously generated custom slices or quickly generate new custom slices using the constituent slices. However, files that are no longer of interest to the user (and hence have not been opened by the user recently) will eventually be deleted from the memory drive 20 as it becomes full.

Multi-Probe Inspection

Figure 12:
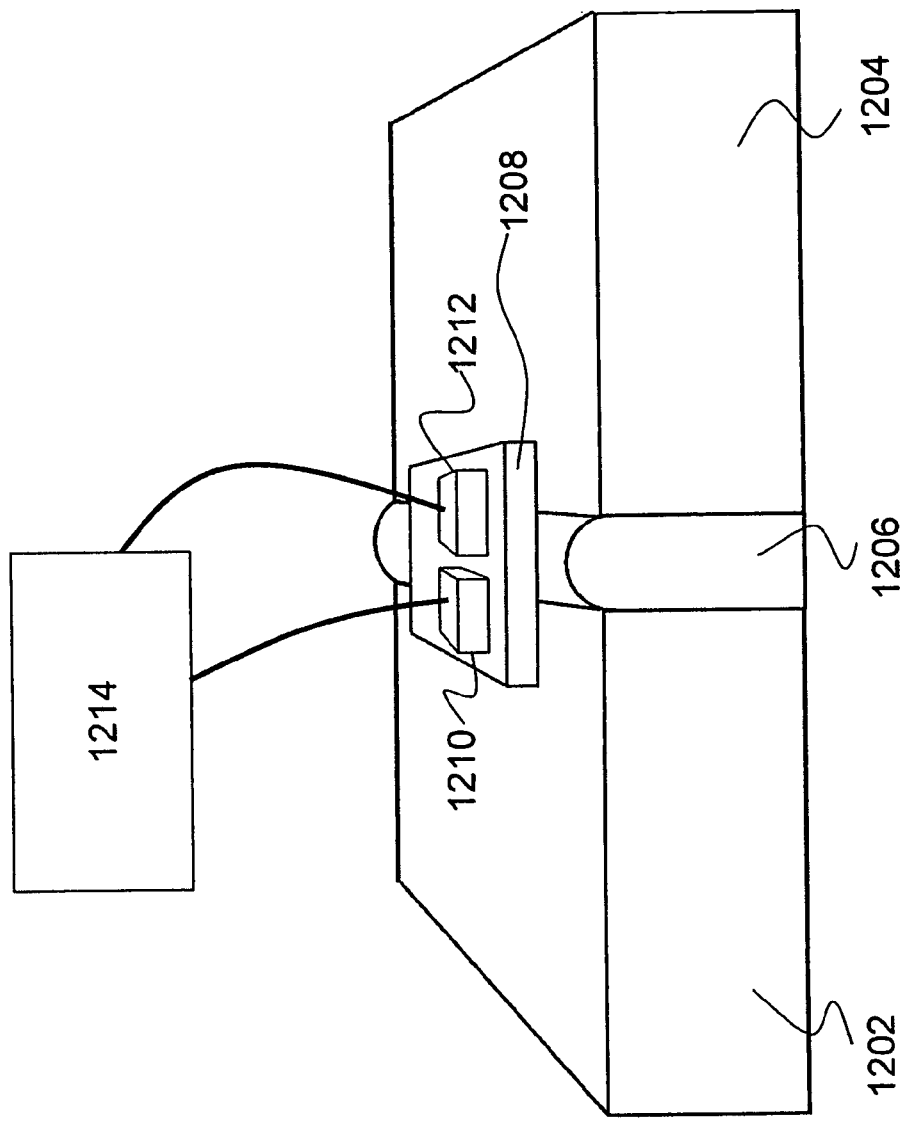
FIG. 12 is a schematic of a multi-probe scanner inspecting a weld between two surfaces.

When scanning a specimen, it is often desirable to perform scanning using a scanner having multiple probes mounted on it. For example, FIG. 12 shows a pair of pipes 1202, 1204, welded together by weld 1206. A multi-probe inspection system employing a scanner 1208 having mounted on it two probes, 1210 and 1212, is used for inspecting the weld 1206 for any cracks or other flaws. The probes 1210, 1212 are electrically connected to device 1214, which controls the scanning and analyses the data collected during the inspection. A mechanical robot (not shown) or equivalent apparatus moves the scanner 1208, and hence the probes 1210, 1212 in fixed relation to each other during the scanning process in order to ensure adequate data is collected to fully inspect the weld.

Figure 13:
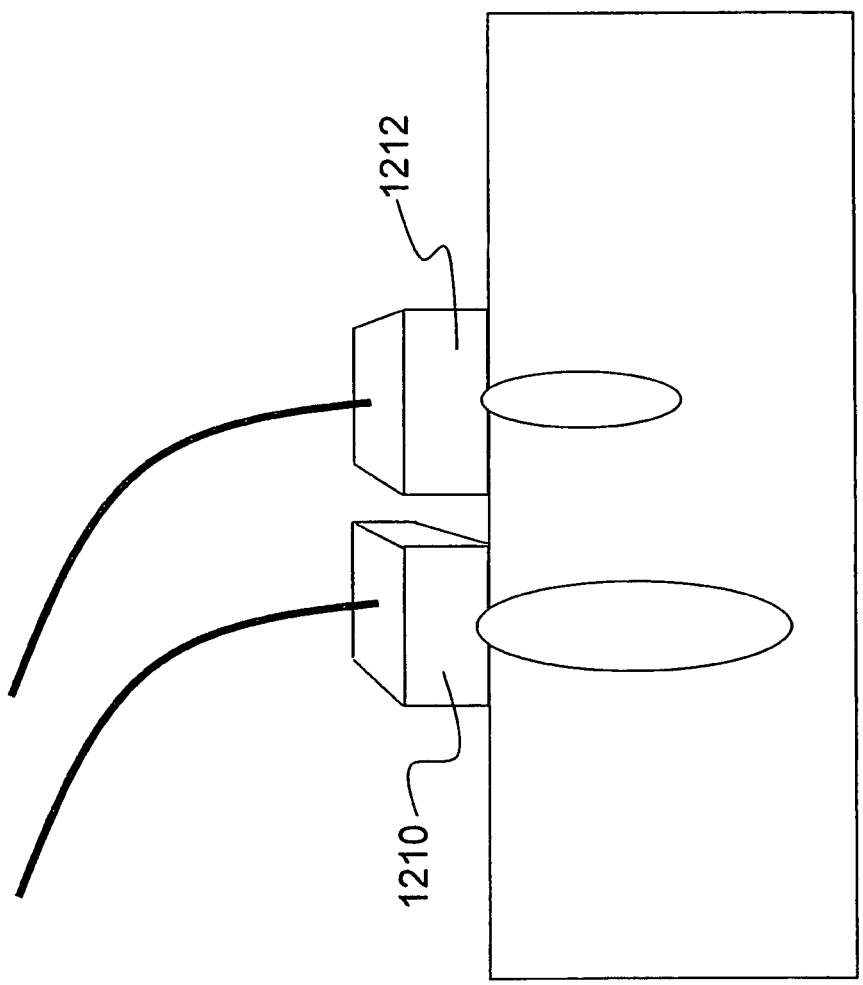
FIG. 13 is a schematic demonstrating two probes with different beam sizes.

Currently, in a multi-probe system such as that shown in FIG. 12, it may be the case that the footprint of probe 1210 is different from probe 1212. For example, assuming the probes are phased array probes, probe 1210 may have a different number of elements from probe 1212, or the elements may be arranged in a different pattern. Additionally, probe 1210 may have a different probe shadow or a different beam size from probe 1212. For example, consider FIG. 13. The ultrasonic zone of interest for probe 1210 is deeper in the material than probe 1212, and the beam of probe 1210 spans a wider volume. In other words, probe 1210 fires a deeper and larger ultrasonic beam. This translates to a longer acquisition time and hence a slower acquisition rate. For example, the acquisition rate may be 2000 Hz for probe 1210 and 5000 Hz for probe 1212. In other words, it may take 0.5 ms to acquire the data from probe 1210, but only 0.2 ms to acquire the data from probe 1212.

In current systems, regardless of whether probes 1210 and 1212 are different or identical, the probes are fired with the same firing frequency. It has been recognized that in multi-probe systems in which probes having different beam sizes are used, a probe with a larger beam size may be fired proportionally less frequently than a probe with a smaller beam size. In other words, if two probes having a smaller beam size and larger beam size respectively are moved at the same rate, as they would be when fixedly mounted on a scanner, the probe with the larger beam size does not need to be fired as often since it covers more volume (i.e. has a larger beam size which spans a larger area) for a given acquisition cycle. By firing probe 1210 less frequently, this results in less data acquisition and data storage and processing by device 1214. However, inspection performance is not sacrificed because only the redundant firings of probe 1210 are eliminated. In firing probes 1210 and 1212 at the same frequency, there is an unnecessary amount of overlap in the adjacent firings of probe 1210 since it has a larger beam size than probe 1212. It is these overlap or redundant firings that are eliminated by having the larger probe fire less frequently.

Figure 14:
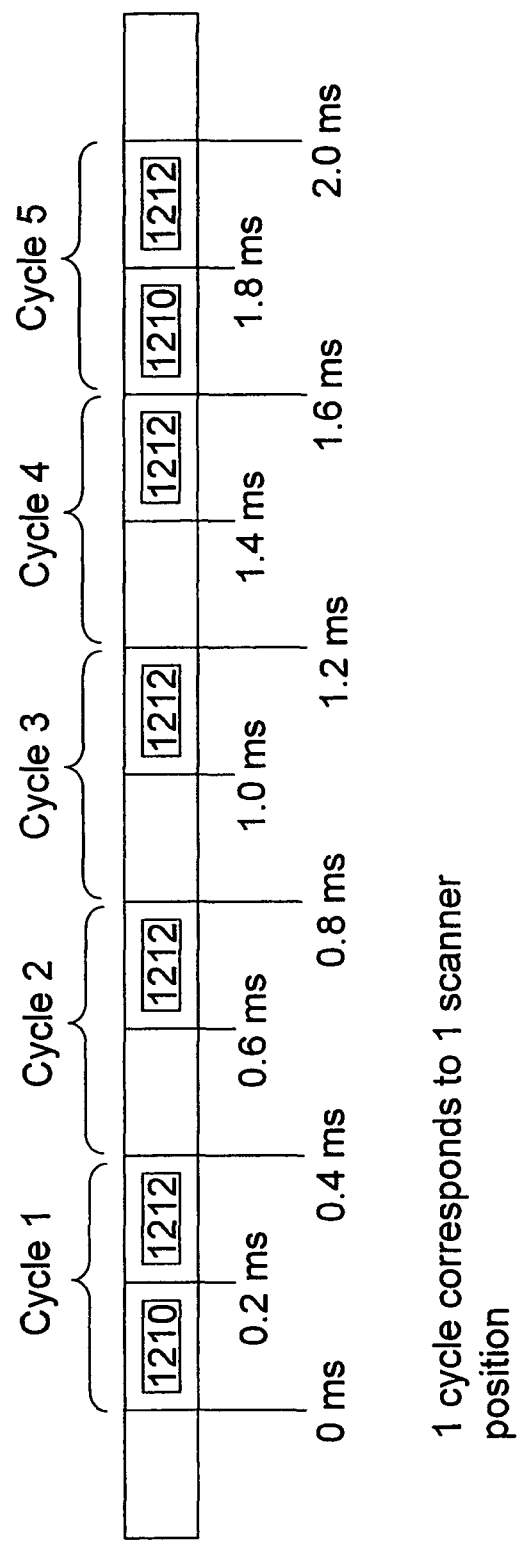
FIG. 14 discloses an example of a firing scheme in which two probes have different firing frequencies.

Consider the following example, which demonstrates one possible embodiment of the above method of utilizing independent and different firing frequencies for each probe. Let us suppose, for example, that probe 1210 has a relatively large beam and therefore has an acquisition time of 0.5 ms. Of the 0.5 ms, let us suppose 0.2 ms is dedicated to the time it takes the beam to be generated and to propagate in the material and return useful echo data, and 0.3 ms is dedicated to the time the probe must additionally wait for the fired sound wave to attenuate in the material (since the wave will persist and rebound in the specimen after the useful echo data has been collected, which generates noise). We will assume a negligible amount of time is dedicated to any overhead related to collecting and managing the data. Let us also suppose that probe 1212 has a beam that covers a smaller volume than probe 1210 and therefore has an acquisition time of 0.2 ms. Of the 0.2 ms, 0.05 ms is dedicated to the time it takes the beam to be generated and useful echo data to be received, and 0.15 ms is dedicated to the time the probe must additionally wait for the fired sound wave to attenuate in the material. Again, we will assume that a negligible amount of time is dedicated to overhead. In current systems, each acquisition cycle would take 0.7 ms. That is, the scanner would move to a first position, fire probe 1210 (0.5 ms) then fire probe 1212 (0.2 ms), and then move to the next scanner position and repeat. The acquisition time for each position is therefore 0.5 ms+0.2 ms=0.7 ms. Since probe 1210 is fired as often as probe 1212 (i.e. once per cycle, that is once per scanner position), redundant data is being collected by probe 1210 because it has a larger beam width that spreads across a number of neighbouring scanner positions. As described above, it has been recognized that the total acquisition time for each position can be reduced by eliminating the redundant firings of probe 1210. Specifically, in this example and with reference to FIG. 14, during the first cycle (i.e. the first scanner position) at time 0 ms, probe 1210 fires and then 0.2 ms later (the amount of time it takes for probe 1210 to receive the useful echo data) probe 1212 fires. Probe 1212 takes 0.2 ms to receive the useful echo data and allow for the fired wave to attenuate in the material. Therefore, at time 0.4 ms, the scanner moves to a second position. During this cycle only probe 1212 fires. It is not necessary for probe 1210 to fire again since the second scanner position was covered by the first firing of probe 1210. Therefore, 0.2 ms later, the scanner is able to move again; however, to simplify this implementation, in an exemplary embodiment the time between scanner movements is set at 0.4 ms, which is the amount of time it takes to acquire data at a scanner position in which both probes fire. Therefore, at 0.8 ms, the scanner moves again to a third position and only probe 1212 is fired, assuming probe 1210 also covered this volume in its first firing. In this way, the scanner moves to each new position every 0.4 ms. This is a reduction compared to 0.7 ms per position because the time it takes probe 1210 to acquire useful echo data (only the 0.2 ms of the 0.5 ms) and the larger size of the beam emitted by probe 1210 has been integrated into the firing frequency calculation, and the firing frequency of probe 1210 has been reduced. Of course, once probe 1210 needs to fire again (say for example at 1.6 ms if we assume probe 1210 needs to be fired only one quarter as often as probe 1212) sufficient time has passed to allow the full 0.5 ms required between firings of probe 1210.

The above is a simplified embodiment to assist in explaining the implementation of independent and different firing frequencies for each probe to allow for faster data acquisition and to eliminate the unnecessary acquisition of redundant data. For example, it was assumed that there were only two probes, that overhead time was negligible, and that only one beam was fired per probe during each acquisition (instead of a set of focal laws). However, the above example demonstrates that critical parameters such as the size of each probe and the size of each beam are necessary in the calculation of the different firing frequencies. Other parameters, such as the frequency of the crystal(s) in the probe and the attenuation time in the inspected material will also need to be factored into the calculation.

Figure 15:
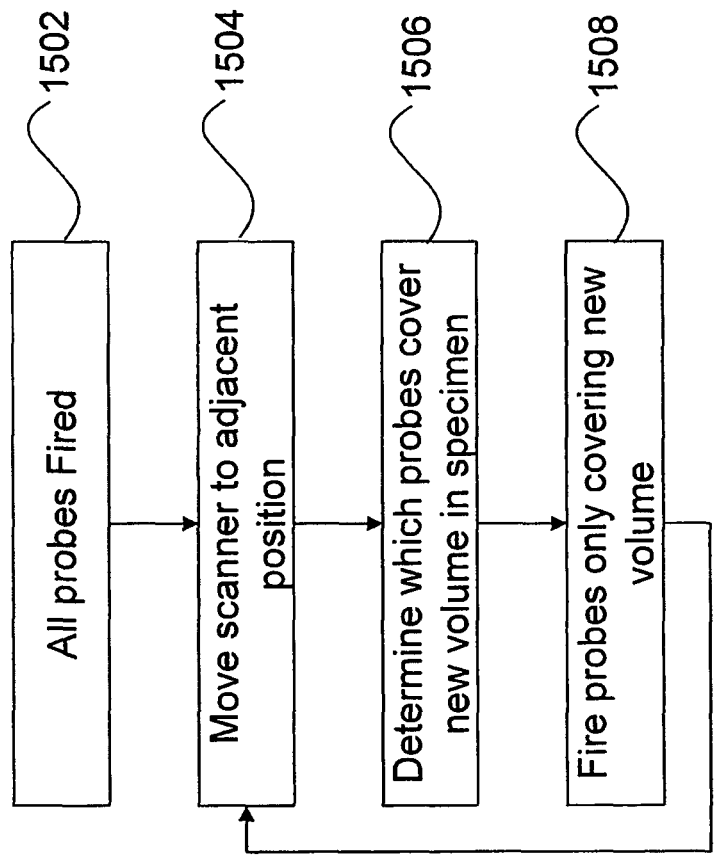
FIG. 15 is a schematic diagram of a set of computer executable instructions for an embodiment of a method of independently firing multiple probes.

As a summary, FIG. 15 shows a general embodiment of a method of applying independent or different firing frequencies for each of N probes. In this figure, a set of computer readable instructions is shown that are stored in module 24f, which is responsible for multi-probe firing.

Recall that only a portion of a probe's acquisition time is dedicated to firing the focal laws and receiving the relevant echo data. With reference to FIG. 15, this portion of time will be referred to as the "first portion" of the acquisition time. The other portion of the acquisition time is dedicated to allowing the sound waves to attenuate (to avoid noise during subsequent firing), as well as for overhead. This portion of the acquisition time will be referred to as the "second portion". Also, with reference to FIG. 15, sequential firing will be assumed; however, it will be appreciated that the method can also be extended to parallel firing of multiple probes, that is when two or more probes fire at the same time instead of in sequence.

Initially, in step 1502, all N probes mounted on the scanner are fired in sequence. The duration of time between the firing of each probe is equal to the first portion of time for each probe. However, after the firing of the last probe, the scanner does not move to an adjacent position until the end of the second portion of time of the last probe. Preferably, the last probe in the firing sequence is the probe with the shortest acquisition time. Waiting to the end of the second portion of time allows the last probe to be fired again once the scanner has moved to its adjacent position. The maximum acquisition time of each cycle (i.e. each scanner position) is a cycle when each probe fires and is calculated as the summation of the first portion of times for each probe added to the second portion of time of the last probe. For example, if there were three probes, the maximum acquisition time would be:

$$\text{acquisition time} = P1_{first} + P2_{first} + P3_{first} + P3_{second}.$$

In step 1504, the scanner is then moved to an adjacent position. In step 1506, for each probe on the scanner, it is determined whether this new adjacent probe position now covers new volume in the specimen not covered in the previous firing of the probe. In step 1508, only probes are fired for which new volume in the specimen is covered. The scanner then moves to an adjacent position after the duration of the maximum acquisition time and steps 1506 and 1508 are repeated until scanning of the device is complete. In this way, each probe has its own firing frequency that ensures no redundant data is collected, and the scanner moves from one position to the next more quickly. Since probes with larger beam sizes are not fired at every scanner position, the amount of time spent at each scanner position can be reduced.

In the an exemplary embodiment, the user calculates and provides the rate at which each probe is to be fired. In an alternative embodiment, the user specifies the beam width of each probe, which is used to derive the frequency in which each probe should be fired. In either case, preferably a "list" or the like is generated by module 24f and stored in memory indicating by way of flags which probes are to be fired at each scanner position. Therefore, during the scanning, the module 24f simply refers to this list and fires the appropriate probes at each scanner position.

Parallel Firing of Multi-Probes

A multi-probe system, such as that shown in FIG. 12, may allow two or more probes to be fired in parallel, that is, at the same time. It will be appreciated that to implement a system having probes that fire in parallel, the data throughput of the system should be able to accommodate the increased throughput of data resulting from the parallel firing of the probes. Also, it will be appreciated that in systems that utilize parallel firing, it is desired to orient the probes such that the emitted beams of each probe interact with each other minimally.

In prior systems, implementing the parallel firing of multiple probes has been a problem due to having only a single digitizer associated with the scanning system. The digitizer performs the function of converting a received analog echo into a digital signal. For example, in a phased array probe, each element receives the returned signal and delays the signal according to the programmed focal law. The received signal from each element is then combined or summed to form the received echo, and this is sent to the digitizer to be converted into digital form. However, if two probes are fired in parallel, the received echo for each probe may arrive at the digitizer at the same time. In this case, either the digitizer is forced to ignore (and hence discard) the received echo from one of the probes, or both of the received echos will be superimposed and added to each other, therefore corrupting both signals.

Figure 16:
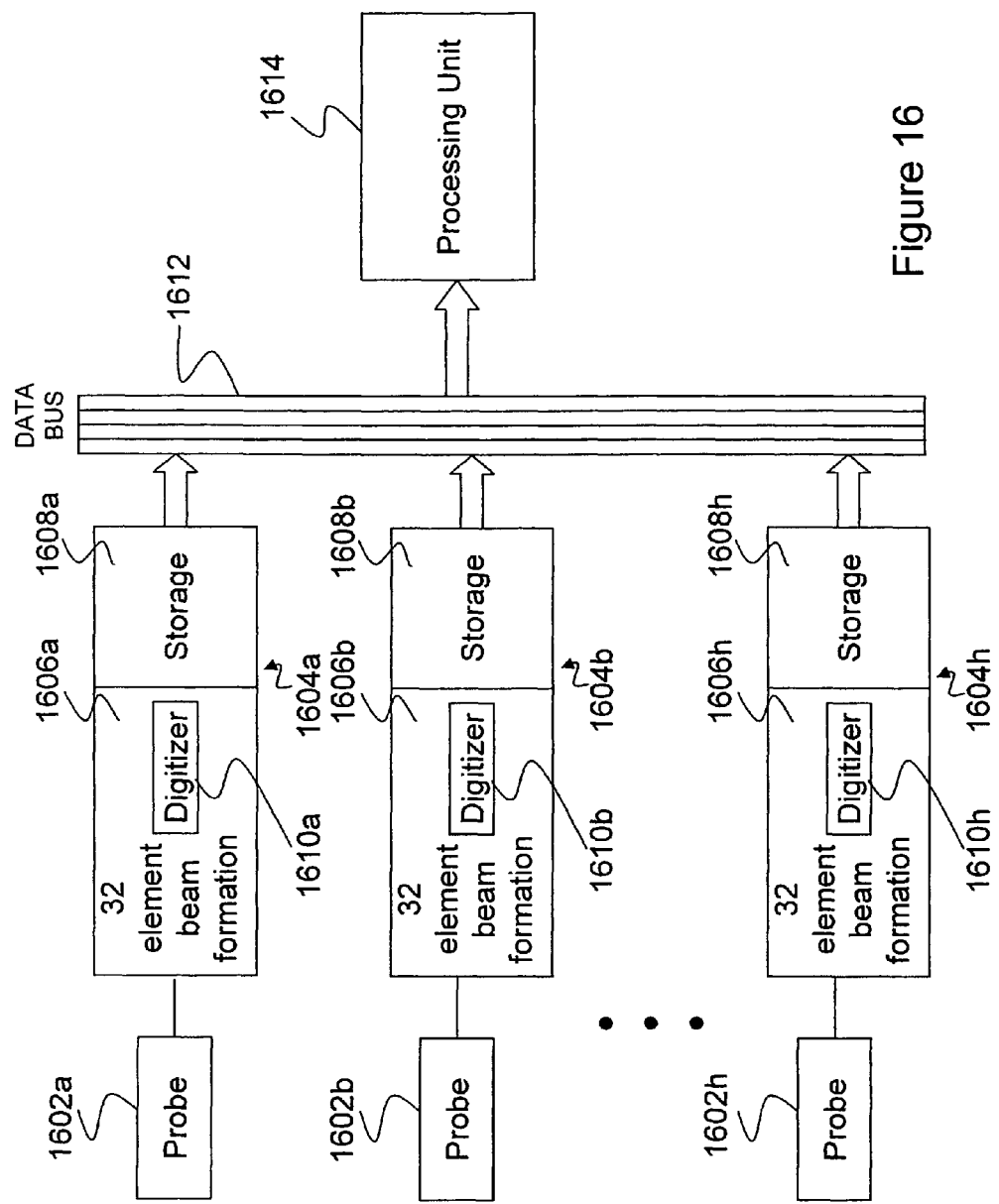
FIG. 16 is a schematic of an embodiment of a system for implementing parallel firing.

FIG. 16 shows an embodiment of a system for implementing parallel firing that obviates or mitigates the above described scenario. Such a system utilizes the concept of modularity to make the storage and processing of data collected in parallel by the multiple probes simple and efficient. In the embodiment shown in FIG. 16, there is assumed to be eight phased-array probes, each of which have 32 elements. It will be appreciated that the number of probes and/or number of elements for each probe may be different depending on the application of the ultrasonic testing equipment.

As shown in FIG. 16, each probe 1602a, 1602b, . . . is associated with its own independent module 1604a, 1604b, . . . A given module 1604a comprises a first unit 1606a for firing probe 1602a according to the programmed focal laws stored in the first unit 1606a and for receiving the returned echo data, and a second unit 1608a for storing the returned echo data to be processed. The first unit 1606a includes its own digitizer 1610a for converting the received echo into a digital signal. This digital data is then stored in storage 1608a. Each module 1604a, 1604b, . . . is electrically connected to a bus 1612, which also connects to a processing unit 1614. Each module 1604a, 1604b, . . . operates independent of the other modules.

In use, two or more of the probes 1602a, 1602b, . . . are first fired in parallel. The returned data from each probe is independently collected and digitized, and the received digital signal is locally stored until the processing unit 1614 is ready to process it. Generally, the processing unit 1614 processes the data from each probe sequentially. For example, if probes 1602a and 1602b were fired in parallel, after data collection and storage, the received data stored in unit 1608a would first be placed on the bus 1612 and read by processing unit 1614. Subsequently, the received data stored in unit 1608b would then be placed on the bus 1612 to be read by the processing unit 1614. The amount of time for the processing unit 1614 to sequentially read the data from each probe is overhead time to be factored into the acquisition time of each probe (e.g. it would be included in the "second portion" of acquisition time described with reference to FIG. 15).

Advantageously, the bus 1612 additionally includes summation functionality (not shown) that allows the digital signals from any number of storage units 1608a, 1608b, . . . to be summed. Such a feature would be utilized when a probe is being used with more elements than supported by a single module. As an example, in the embodiment shown in FIG. 16, each module 1604a, 1604b, . . . can support a maximum of 32 elements. If the application used a 64 element probe, module 1604a could be associated with elements 1 to 32, and module 1604b could be associated with elements 33 to 64. Modules 1604a and 1604b would then each independently collect and digitize the data received by elements 1 to 32 and elements 33 to 64 respectively. Using the bus 1612, the partial sums from elements 1 to 32 and 33 to 64 could then be summed (in the manner indicated by the focal law) and the resulting signal could be stored in either storage unit 1608a or 1608b.

A modular structure with bus summation capabilities, such as that described above, allows parallel firing to be implemented efficiently and effectively.

Although the invention has been described with reference to certain specific embodiments, various modifications thereof will be apparent to those skilled in the art without departing from the spirit and scope of the invention as outlined in the claims appended hereto.

What is claimed is:

1. A method of establishing position dependent focal laws for the ultrasonic inspection of a specimen with complex geometry, said method being performed by a computing device and comprising:
    (a) creating a computer model fully describing the geometry of the specimen;
    (b) partitioning said model into distinct first and second regions
        wherein said first region has different geometric characteristics than said second region
        said first region comprising sub-regions each sub-region having distinct irregular geometric characteristics from at least one other of the sub-regions in said first region
        said second region comprising sub-regions each sub-region having distinct irregular geometric characteristics from at least one other of the sub-regions in said second region
    (c) determining a first set of focal laws for use with said first region, said first set of focal laws approximately accommodating said distinct irregular geometric characteristics of said sub-regions in said first region
    (d) determining a second set of focal laws for use with said second region, said second set of focal laws approximately accommodating said distinct irregular geometric characteristics of said sub-regions in said second region
    (e) associating each position of a scanner with at least one of said first or second regions and storing the association in memory; and
    (f) positioning said scanner to a portion of the specimen within said first region and applying said set of focal laws associated with said first region
    (g) repositioning said scanner to a portion the specimen within said second region and applying said second set of focal laws associated with said second region.

2. A method of establishing position dependent focal laws for the ultrasonic inspection of a specimen with complex geometry, said method being performed by a computing device and comprising (a) loading a computer model of said specimen into a portion of memory;
(b) partitioning said model into distinct regions;
(c) generating a distinct set of focal laws for each of said distinct regions;
(d) associating each position of a scanner with at least one of said distinct regions and storing the association in memory; and
(e) during subsequent ultrasonic inspection of said specimen, enabling each position of said scanner to use said distinct set of focal laws associated with said at least one region wherein partitioning said model into distinct regions comprises:
(i) characterizing a surface corresponding to a first scanner position on said model, and designating this surface as belonging to a first region;
(ii) characterizing each of the surfaces corresponding to all other scanner positions on said model;
(iii) using a defined measure of difference between surface characteristics to calculate a set of error values, each error value representing a difference in surface characteristics between one of the surfaces in said all other scanner positions and the surface in said first scanner position;
(iv) selecting a second scanner position from said all other scanner positions, said second scanner position being the scanner position having the largest error value; and
(v) designating the surface corresponding to the second scanner position as belonging to said second region.

3. The method of claim 2 wherein characterizing a surface comprises generating an elevation matrix having dimensions spanning an area defined by a probe shadow of a probe on said scanner and storing in the matrix numbers representing the elevation of the surface spanned.

4. The method of claim 3 wherein said model is a computer-aided-design (CAD) model and wherein the area defined by the probe shadow corresponds to an area defined by a set of focal laws.

5. A method of establishing position dependent focal laws for the ultrasonic inspection of a specimen with complex geometry, said method being performed by a computing device and comprising
(a) loading a computer model of said specimen into a portion of memory;
(b) partitioning said model into distinct regions;
(c) generating a distinct set of focal laws for each of said distinct regions;
(d) associating each position of a scanner with at least one of said distinct regions and storing the association in memory; and
(e) during subsequent ultrasonic inspection of said specimen, enabling each position of said scanner to use said distinct set of focal laws associated with said at least one region
wherein said model is a computer-aided-design (CAD) model and wherein said partitioning said model into distinct regions comprises:
(i) establishing an initial geometric region on the CAD model associated with an initial scanner position;
(ii) using a data structure to characterize a surface of said initial region;
(iii) storing a set of reference data structures, said set including said data structure characterizing the surface of said initial region;
(iv) selecting a neighbouring scanner position in the CAD model;
(v) using a data structure to characterize a surface of said neighbouring scanner position;
(vi) comparing the data structure characterizing the surface of said neighbouring scanner position with each reference data structure and calculating for each reference data structure an error representing a measure of difference between the surface of said neighbouring scanner position and the surface of the region characterized by the reference data structure;
(vii) selecting the smallest of the error values calculated in operation (vi) and storing this value as the surface error associated with said neighbouring scanner position;
(viii) repeating operations (iv) to (vii) for each scanner position;
(ix) choosing as a new geometric region the scanner position with the largest surface error;
(x) adding to said set of reference data structures a data structure characterizing the surface of said new geometric region; and
(xi) returning to said initial scanner position and repeating operations (iv) to (x) until a designated maximum number of new geometric regions has been generated or until a request is received to terminate the method.

6. The method of claim 5 wherein each one of the data structures is a matrix representing the elevation of the surface over an area defined by a probe shadow of a probe on said scanner.

7. The method of claim 6 wherein associating each position of a scanner with at least one of said distinct regions and storing the association in memory comprises:
(A) selecting a first scanner position in the CAD model;
(B) comparing the data structure characterizing the surface of the first scanner position with each reference data structure and calculating for each reference data structure an error representing a measure of difference between the surface of said first scanner position and the surface of the region characterized by the reference data structure;
(C) selecting the reference data structure resulting in the smallest of the error values calculated in step (B) and associating in memory the first scanner position with the region characterized by this reference data structure; and
(D) repeating operations (A) to (D) for each scanner position.

8. The method of claim 6 wherein said designated maximum number of new geometric regions is derived from the maximum number of focal laws the computing device can store, and wherein a request is generated to terminate operations (iv) to (x) when the surface error for each scanner position is zero.

9. The method of claim 6 wherein each matrix stores between 16 and 256 points.

10. The method of claim 6 wherein said error of step (vi) representing a measure of difference between the surface of said neighbouring scanner position and the surface of the region characterized by the reference data structure is calculated as $$\text{error} = \sqrt{\frac{1}{n} \sum_{i,j} (a_{ij} - b_{ij})^2},$$

where $a_{ij}$ and $b_{ij}$ respectively represent points in the matrix representing the elevation of the surface of the neighbouring scanner position and the reference matrix, and n is the size of each matrix.

11. A computing device, said computing device comprising:
- a processor;
- a communicable connection to a scanner;
- a memory; and
- a set of computer executable instructions for establishing position dependent focal laws for the ultrasonic inspection of a specimen with complex geometry, said computer executable instructions comprising instructions for:
  - (a) creating a computer model fully describing the geometry of the specimen;
  - (b) partitioning said model into distinct first and second regions
    - wherein said first region has different geometric characteristics than said second region
    - said first region comprising sub-regions each sub-region having distinct irregular geometric characteristics from at least one other of the sub-regions in said first region
    - said second region comprising sub-regions each sub-region having distinct irregular geometric characteristics from at least one other of the sub-regions in said second region
  - (c) determining a first set of focal laws for use with said first region, said first set of focal laws approximately accommodating said distinct irregular geometric characteristics of said sub-regions in said first region
  - (d) determining a second set of focal laws for use with said second region, said second set of focal laws approximately accommodating said distinct irregular geometric characteristics of said sub-regions in said second region
  - (e) associating each position of a scanner with at least one of said first or second regions and storing the association in memory; and
  - (f) positioning said scanner to a portion of the specimen within said first region and applying said set of focal laws associated with said first region
  - (g) repositioning said scanner to a portion the specimen within said second region and applying said second set of focal laws associated with said second region.

12. A non-transitory computer readable medium having stored thereon computer-executable instructions for establishing position dependent focal laws for the ultrasonic inspection of a specimen with complex geometry, said computer executable instructions comprising instructions for:
- (a) creating a computer model fully describing the geometry of the specimen;
- (b) partitioning said model into distinct first and second regions
  - wherein said first region has different geometric characteristics than said second region
  - said first region comprising sub-regions each sub-region having distinct irregular geometric characteristics from at least one other of the sub-regions in said first region
  - said second region comprising sub-regions each sub-region having distinct irregular geometric characteristics from at least one other of the sub-regions in said second region
- (c) determining a first set of focal laws for use with said first region, said first set of focal laws approximately accommodating said distinct irregular geometric characteristics of said sub-regions in said first region
- (d) determining a second set of focal laws for use with said second region, said second set of focal laws approximately accommodating said distinct irregular geometric characteristics of said sub-regions in said second region
- (e) associating each position of a scanner with at least one of said first or second regions and storing the association in memory; and
- (f) positioning said scanner to a portion of the specimen within said first region and applying said set of focal laws associated with said first region
- (g) repositioning said scanner to a portion the specimen within said second region and applying said second set of focal laws associated with said second region.

* * * * *